US012733908B2

(12) United States Patent
Schaer et al.

(10) Patent No.: US 12,733,908 B2
(45) Date of Patent: Sep. 15, 2026

(54) CABLE ROUTING AND ASSEMBLIES FOR MEDICAL DEVICE HANDLES

(71) Applicant: NUVERA MEDICAL, INC., Los Gatos, CA (US)

(72) Inventors: Alan Schaer, San Jose, CA (US); Jerry Hopple, Seabeck, WA (US); Daniel Lundberg, Los Gatos, CA (US); Tomas Robinson, Santa Clara, CA (US); Colin Mixter, Los Gatos, CA (US)

(73) Assignee: NuVera Medical, Inc., Los Gatos, CA (US)

( * ) Notice: Subject to any disclaimer, the term of this patent is extended or adjusted under 35 U.S.C. 154(b) by 211 days.

(21) Appl. No.: 17/776,398

(22) PCT Filed: Nov. 25, 2020

(86) PCT No.: PCT/US2020/062244
§ 371 (c)(1),
(2) Date: May 12, 2022

(87) PCT Pub. No.: WO2021/108562
PCT Pub. Date: Jun. 3, 2021

(65) Prior Publication Data

US 2022/0401070 A1 Dec. 22, 2022

Related U.S. Application Data

(60) Provisional application No. 62/941,435, filed on Nov. 27, 2019.

(51) Int. Cl.
*A61B 8/00* (2006.01)
*A61B 8/12* (2006.01)
(Continued)

(52) U.S. Cl.
CPC ................ *A61B 8/445* (2013.01); *A61B 8/12* (2013.01); *H01B 7/048* (2013.01);
(Continued)

(58) Field of Classification Search
CPC ..... A61B 8/445; A61B 8/12; A61B 2562/182; A61B 2562/222; A61B 8/4438;
(Continued)

(56) References Cited

U.S. PATENT DOCUMENTS 4,615,330 A 10/1986 Nagasaki et al.
5,543,831 A 8/1996 Tsuji et al.
(Continued)

FOREIGN PATENT DOCUMENTS

JP 04-183432 A 6/1992
JP 08-211307 A 8/1996
(Continued)

OTHER PUBLICATIONS

Translation of JP-2000245734-A, relied upon herein (Year: 2000).*
(Continued)

*Primary Examiner* — Anh Tuan T Nguyen
*Assistant Examiner* — Dean N Edun
(74) *Attorney, Agent, or Firm* — Smith, Gambrell & Russell LLP

(57) ABSTRACT

Medical devices that include a medical tool, a handle and a flexible cable bundle passing through the handle. The handles and cable routing therethrough are adapted to reduce noise within the cable.

22 Claims, 28 Drawing Sheets

(51) Int. Cl.
*H01B 7/04* (2006.01)
*H01B 11/18* (2006.01)

(52) U.S. Cl.
CPC .... *H01B 11/1895* (2013.01); *A61B 2562/182* (2013.01); *A61B 2562/222* (2013.01)

(58) Field of Classification Search
CPC . A61B 8/4466; A61B 8/4494; A61B 1/00124; A61B 1/0057; A61B 1/0052; A61B 8/4483; A61B 18/1492; A61B 8/4461; A61B 1/00114; A61B 1/00018; A61B 2018/00577; A61B 8/4209; A61B 8/4254; A61B 8/4444; A61B 8/4455; A61B 1/00009; A61B 1/00097; H01B 7/048; H01B 11/1895; H01B 11/20; H01B 11/02; H01B 7/17; H01B 7/0009; H01B 7/04; H01B 9/006; H01B 11/06; A61M 25/0136; H01R 13/646; H01R 13/719; H01R 11/18; H01R 12/594; H01R 13/64; H01R 13/6461; H01R 24/40
See application file for complete search history.

(56) References Cited

U.S. PATENT DOCUMENTS 6,054,649 A 4/2000 Uchida et al.
6,100,626 A 8/2000 Frey
6,319,197 B1 11/2001 Tsuji et al.
6,537,217 B1 3/2003 Bjaerum et al.
6,559,389 B1 5/2003 Kornrumpf et al.
6,623,433 B2 9/2003 Webler et al.
7,257,051 B2 8/2007 Thomenius
7,297,118 B2 11/2007 Kristoffersen
7,331,927 B2 2/2008 Steen
7,338,450 B2 3/2008 Kristoffersen
7,451,650 B2 11/2008 Halvorsrod
7,527,591 B2 5/2009 Haugen
7,527,592 B2 5/2009 Haugen
7,569,015 B2 8/2009 Donaldson
7,621,028 B2 11/2009 Gelly
7,731,516 B2 6/2010 Puttinger
7,740,584 B2 6/2010 Donaldson
7,762,954 B2 7/2010 Nix et al.
7,766,833 B2 8/2010 Lee
7,783,339 B2 8/2010 Lee
7,791,252 B2 9/2010 Baumgartner
7,819,802 B2 10/2010 Secora
7,824,335 B2 11/2010 Wodnicki
7,966,058 B2 6/2011 Xue
8,057,397 B2 11/2011 Li
8,096,951 B2 1/2012 Kristoffersen
8,207,652 B2 6/2012 Baumgartner
8,213,693 B1 7/2012 Li
8,364,242 B2 1/2013 Li
8,428,690 B2 4/2013 Li
8,451,155 B2 5/2013 Amemiya
8,527,032 B2 9/2013 Li
8,634,901 B2 1/2014 Callahan et al.
8,659,212 B2 2/2014 Eggen
8,664,938 B2 3/2014 Palassis et al.
8,721,553 B2 5/2014 Lee
8,727,993 B2 5/2014 Lee
8,742,646 B2 6/2014 Wodnicki
8,776,335 B2 7/2014 Baumgartner
8,790,262 B2 7/2014 Li
8,933,613 B2 1/2015 Amemiya
8,978,216 B2 3/2015 Calisti
8,989,842 B2 3/2015 Li
9,055,883 B2 6/2015 Tgavalekos
9,170,132 B2 10/2015 Palassis et al.
9,386,967 B2 7/2016 Miller et al.
9,439,625 B2 9/2016 Cogan
9,575,165 B2 2/2017 Miller
9,639,056 B2 5/2017 Falter
10,292,764 B2 5/2019 Datta
10,359,464 B2 7/2019 Parchak et al.
10,507,317 B2 12/2019 Oliverius et al.
10,722,140 B2 7/2020 Izmirli et al.
10,898,269 B2 1/2021 Jaramaz et al.
11,090,063 B2 8/2021 Jaramaz et al.
11,175,161 B2 11/2021 Muratov et al.
2007/0167827 A1* 7/2007 Masters .................. A61B 8/12 600/463
2007/0287920 A1 12/2007 Sawada et al.
2008/0177175 A1 7/2008 Mottola et al.
2008/0287783 A1 11/2008 Anderson
2008/0306380 A1* 12/2008 Parchak ................ A61B 5/283 324/207.12
2009/0275838 A1* 11/2009 Marshall ................ A61B 8/12 600/463
2011/0098573 A1 4/2011 Thornton et al.
2012/0283570 A1 11/2012 Tegg
2015/0228406 A1 8/2015 Corl et al.
2018/0279994 A1* 10/2018 Schaer ................ A61B 8/0883
2019/0298411 A1 10/2019 Davies et al.
2020/0061340 A1 2/2020 Mixter et al.
2020/0246041 A1 8/2020 Morimoto et al.
2020/0359996 A1 11/2020 Walsh et al.
2022/0133139 A1 5/2022 Mahadevan-Jansen et al.
2023/0165468 A1 6/2023 Mahadevan-Jansen et al.
2025/0255578 A1 8/2025 Shah et al.

FOREIGN PATENT DOCUMENTS

JP 09-043520 A 2/1997
JP 2000-245736 A 9/2000
JP 2000245734 A * 9/2000
JP 2001-104311 A 4/2001
JP 2004-209283 A 7/2004
JP 2009-515607 A 4/2009
WO WO 2018/017717 1/2018
WO WO 2018/182836 10/2018
WO 2020/041716 A1 2/2020
WO 2021/108562 A1 6/2021

OTHER PUBLICATIONS

Palomar Engineers webpage, Slip on Ferrite Beads. Aug. 17, 2017. Accessed via the Wayback Machine on Nov. 19, 2024 (Year: 2017).*
European Search Report and Search Opinion Received for EP Application No. 22185248.6, mailed on Oct. 11, 2022, 6 pages.
International Search Report and Written Opinion received for PCT Patent Application No. PCT/US2020/062244, mailed on Feb. 17, 2021, 9 pages.
U.S. Appl. No. 62/941,435, filed Nov. 27, 2019.
PCT/US2020/062244 filed Nov. 25, 2020.
PCT/US2019/047930 filed Aug. 23, 2019.

* cited by examiner

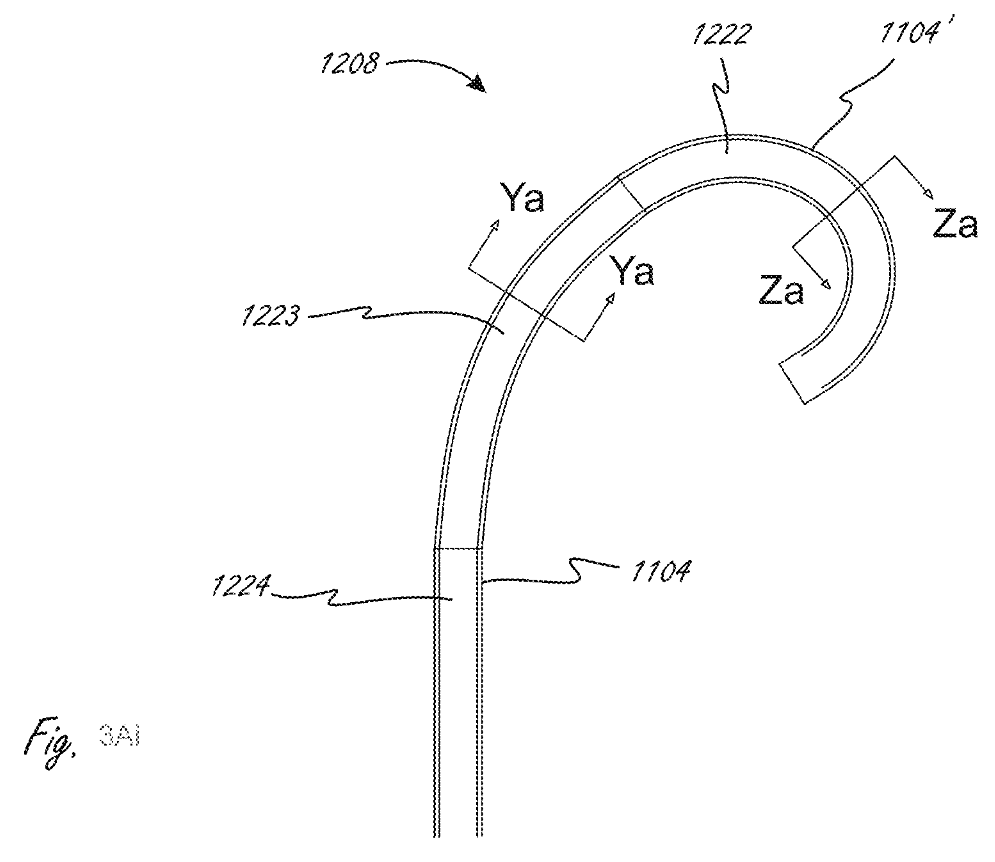
Fig. 3AI
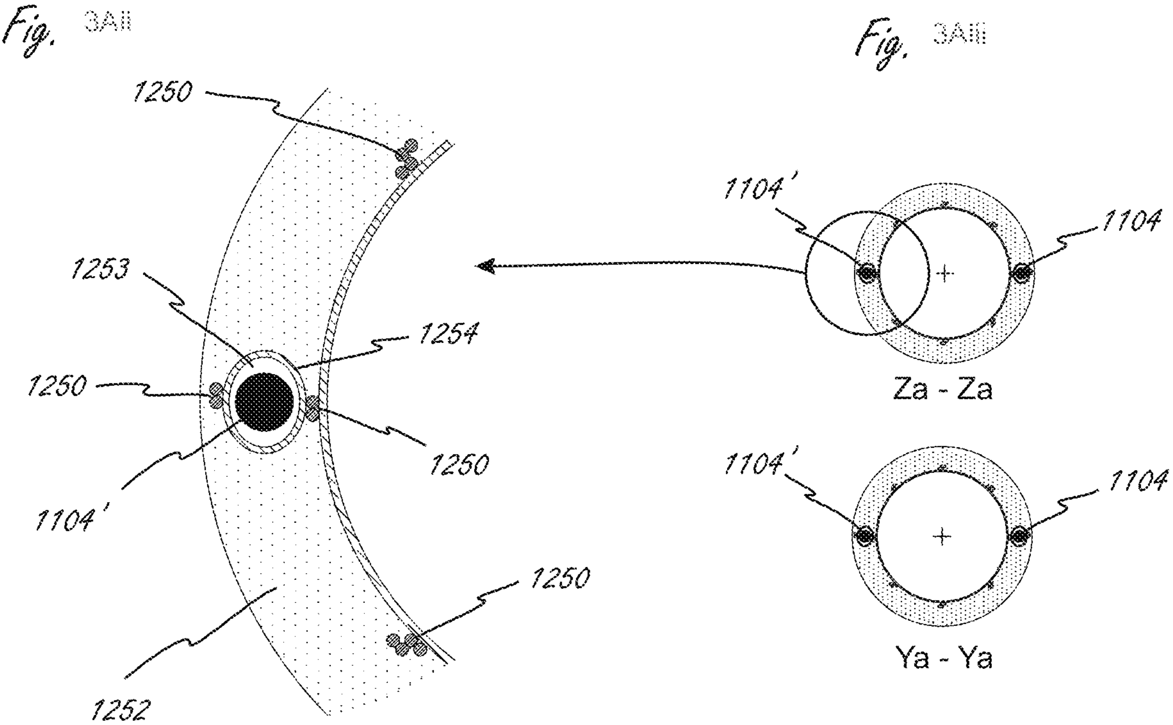
Fig. 3AII
Fig. 3AIII

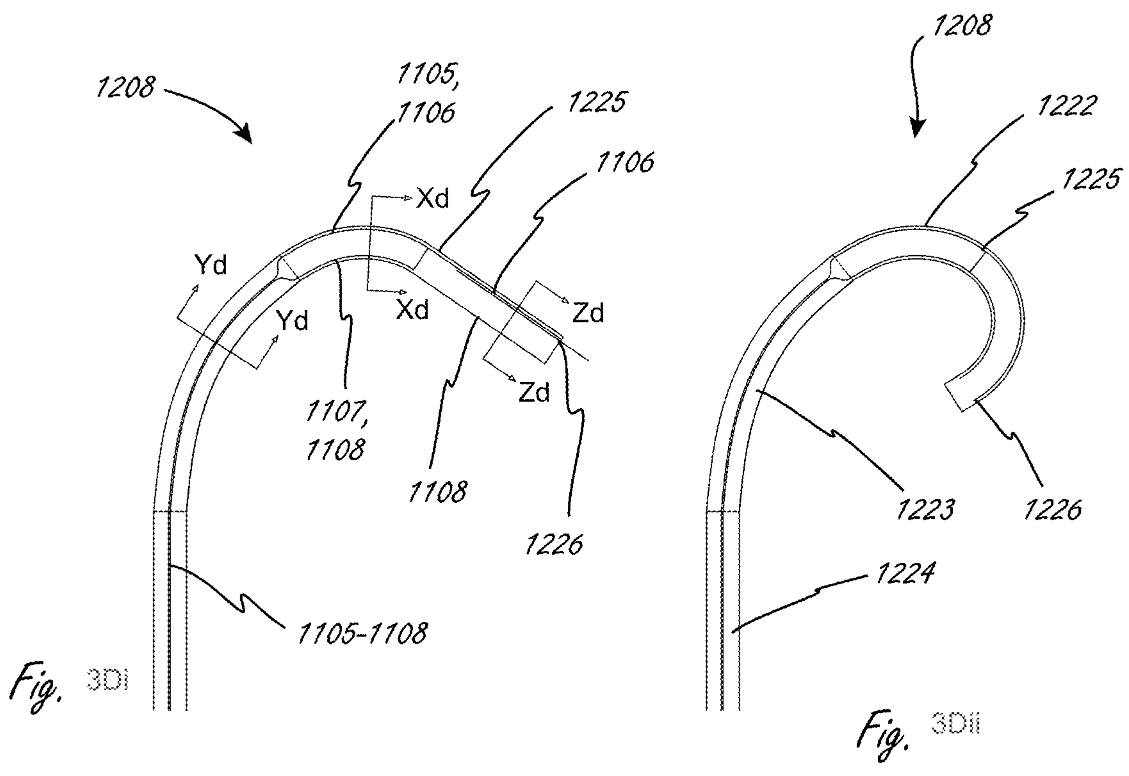
1208
1105,
1106
1225
1106
Xd
Yd
Yd
Xd
Zd
Zd
1107,
1108
1108
1226
1105-1108
Fig. 3Di
1208
1222
1225
1223
1226
1224
Fig. 3Dii
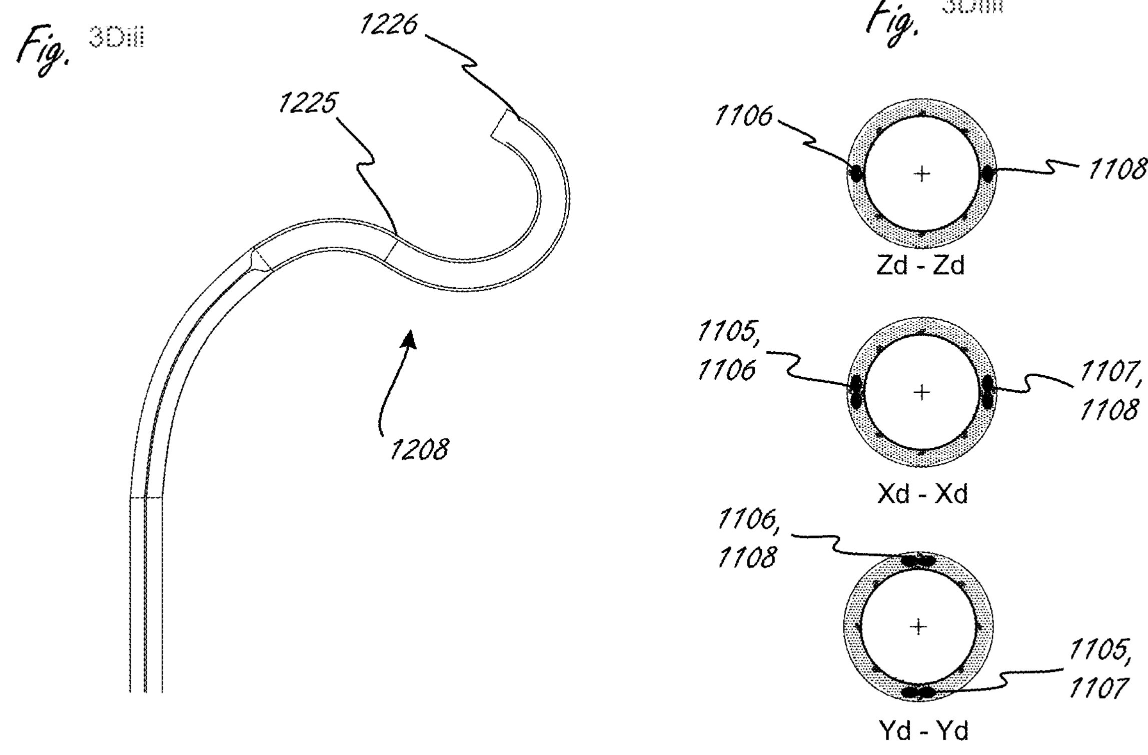
Fig. 3Diii
1226
1225
1208
Fig. 3Diiii
1106
1108
Zd - Zd
1105,
1106
1107,
1108
Xd - Xd
1106,
1108
1105,
1107
Yd - Yd 2020
1212
2010
1208
2020
1821

2070
2050
2024
2015
2030
2031
2021
2020
2060

2021
2026
2023
2022
2024
2024'
2024''
2024'''
2024''''
2020
2022
2023

2024
2026
2021
2025

1200
1202
1204
4000
2070
1215

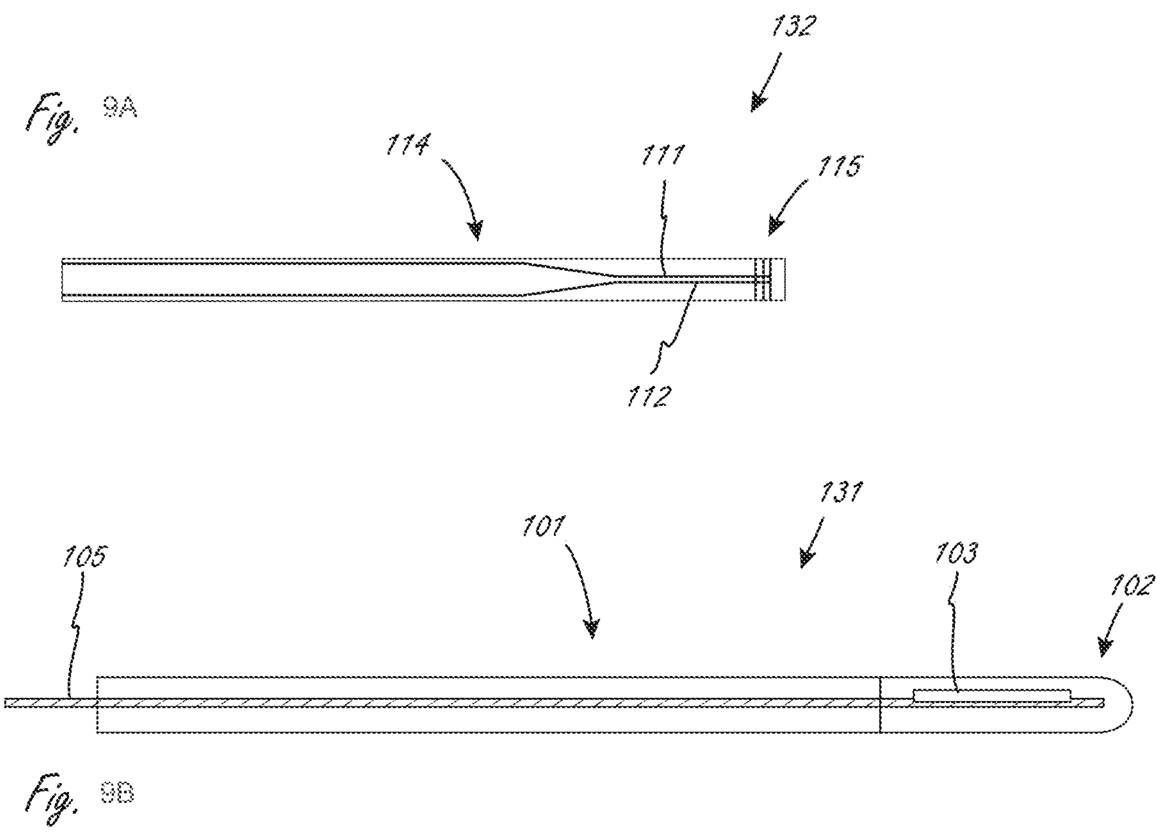
132
Fig. 9A
114
111
115
112
131
101
105
103
102
Fig. 9B
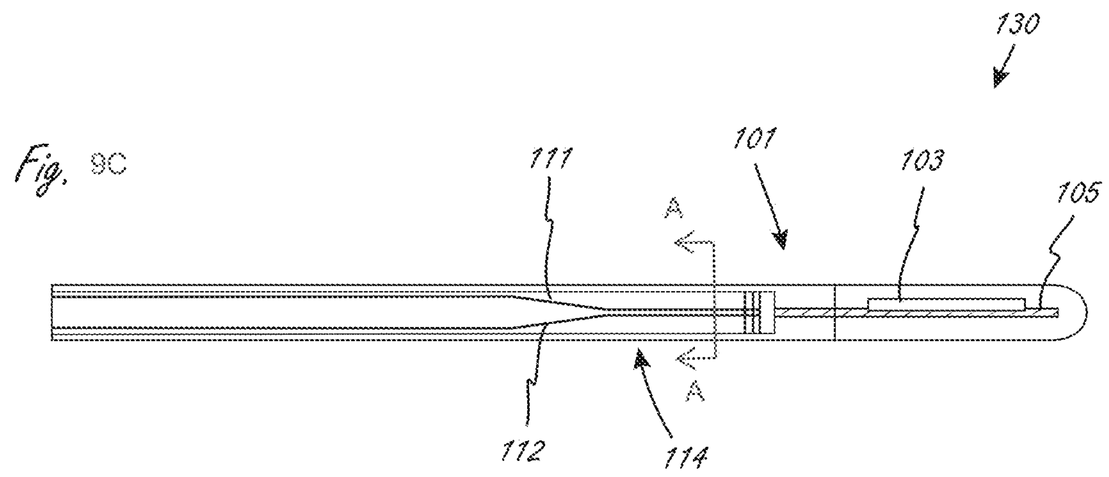
130
Fig. 9C
111
101
103
105
A
A
112
114

SECTION A-A 155
154
161
153
158
162
156
157
152
150
151

LA
181
147
151
142
182
180
141

314
322
310
311
321
312
317
316
320

320
315

316
321
312
320
322
310
314

314
322
310
312
320

332
331
330
333

339
332
336
330
331
111.0cm ± 0.5
338
340
342

332
336
338
330
10.8cm MIN
340
342

332
336
338
330
331
340
342
A

342
DETAIL A
SCALE 7 : 1
1 to 5
6 to 11
12 to 14

1800

Ground
J Power
A Power
Ground
1802
Amphenol
Receptacle Flex
1810
1813
1803
1806
1812

CABLE ROUTING AND ASSEMBLIES FOR MEDICAL DEVICE HANDLES

CROSS-REFERENCE TO RELATED APPLICATIONS

This application is the national stage filing under 35 USC 371 of International Application No. PCT/US2020/062244 filed Nov. 25, 2020, which claims priority to U.S. Provisional Application No. 62/941,435, filed Nov. 27, 2019, which are incorporated by reference herein for all purposes.

The following applications are incorporated by reference herein for all purposes: WO2018/017717, WO 2018/182836 A1, and PCT/US2019/047930.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Medical devices, such as imaging catheters, may include flexible cable bundles extending therethrough that may be susceptible to noise along the cable line(s) in certain frequencies. Cable routing and handle assemblies through which the cables extend may be needed to reduce noise in the cables.

SUMMARY OF THE DISCLOSURE

One aspect of the disclosure is a medical device that includes an elongate shaft sized and configured to be advanced within a patient. The medical device may include a handle sized and positioned to remain outside of the patient, and a flexible elongate cable bundle extending through the elongate shaft and into the handle. Within the handle, one or more shield layers of the cable bundle may be removed from the cable bundle before the remainder of the cable bundle passes through an electrical noise suppression member that is disposed within the handle.

In this embodiment, the medical device may include an ultrasound transducer that is in communication with the flexible cable bundle, optionally wherein ultrasound transducer is disposed in a distal tip of the medical device and optionally wherein the ultrasound transducer is used for medical imaging. The medical device may be used with other energy modalities as well.

In this aspect, the electrical noise suppression member may optionally comprise a ferrite bead.

In this aspect, the flexible cable bundle may be folded upon itself in an organized manner in a folded region within the handle, and wherein the shield layer may have been removed from the cable bundle before the folded region such that the shield layer is not folded within the handle.

In this aspect, the flexible cable bundle may be folded upon itself in an accordion style in a folded region.

In this aspect, the shield layer may be coupled to a receptacle at a proximal end of the handle.

In this aspect, the cable bundle may be coupled to a plurality of printed circuit boards that are secured within the handle, optionally after fanning out from a main cable bundle body.

In this aspect, the cable bundle may extend from a proximal end of an elongate shaft that is disposed within the handle.

In this aspect, the cable bundle may pass by and extend radially outside of a plurality of printed circuit boards that are disposed within the handle.

In this aspect, the cable bundle passes between first and second of a plurality of printed circuit boards that are disposed within the handle.

In this aspect, the cable bundle may include a movable portion that is axially moveable within the handle.

In this aspect, the cable bundle may not be adapted to be moved axially within the handle after the handle is assembled.

In this aspect, the electrical noise suppression member may comprise one or both of a material or configuration adapted to suppress electromagnetic interference from the elongate cable bundle.

In this aspect, the electrical noise suppression member may comprise one or both of a material or configuration to suppress electromagnetic interference into the elongate cable bundle.

One aspect of the disclosure is a medical device that includes an elongate shaft sized and configured to be advanced within a patient. The medical device may include a handle sized and positioned to remain outside of the patient, and a flexible elongate cable bundle extending through the elongate shaft and into the handle.

In this aspect, the flexible elongate cable bundle may be folded upon itself in an organized manner in a folded region within the handle, and wherein a shield layer of the cable bundle is removed from the cable bundle before the folded region such that the shield layer is not folded in the folded region.

This aspect may include any other suitable component, feature or functionality set forth herein, including any other feature of any other aspect in this Summary Section.

In this aspect, the medical device may include an ultrasound transducer that is in communication with the flexible cable bundle, optionally wherein ultrasound transducer is disposed in a distal tip of the medical device and optionally wherein the ultrasound transducer is used for medical imaging.

BRIEF DESCRIPTION OF THE FIGURES

FIGS. 3Ai, 3Aii and 3Aiii illustrate an exemplary steerable shaft with pull wires.

FIGS. 3Di-3Diiii illustrate an exemplary steerable shaft with pull wires.

FIG. 9A illustrates a portion of an exemplary inner elongate body, or inner shaft.

FIG. 9B illustrates a portion of an exemplary outer elongate body, or outer shaft.

FIG. 9C illustrates a portion of an exemplary medical device including the elongate bodies (or shafts) from FIGS. 9A and 9B.

FIGS. 14A and 14B illustrate an exemplary handle that includes a cable bundle shield layer removed before the bundle passes through a ferrite bead.

DETAILED DESCRIPTION

The disclosure herein is related to cable routing and handle assemblies of medical devices that are configured and adapted to improve emission and/or immunity performance. FIGS. 1-13E and the textual descriptions thereof illustrate exemplary features of imaging devices, systems, and methods of use, any of which may be incorporated with the cable routing concepts set forth herein with respect to FIGS. 14A-20.

Figures 1A, 1B:
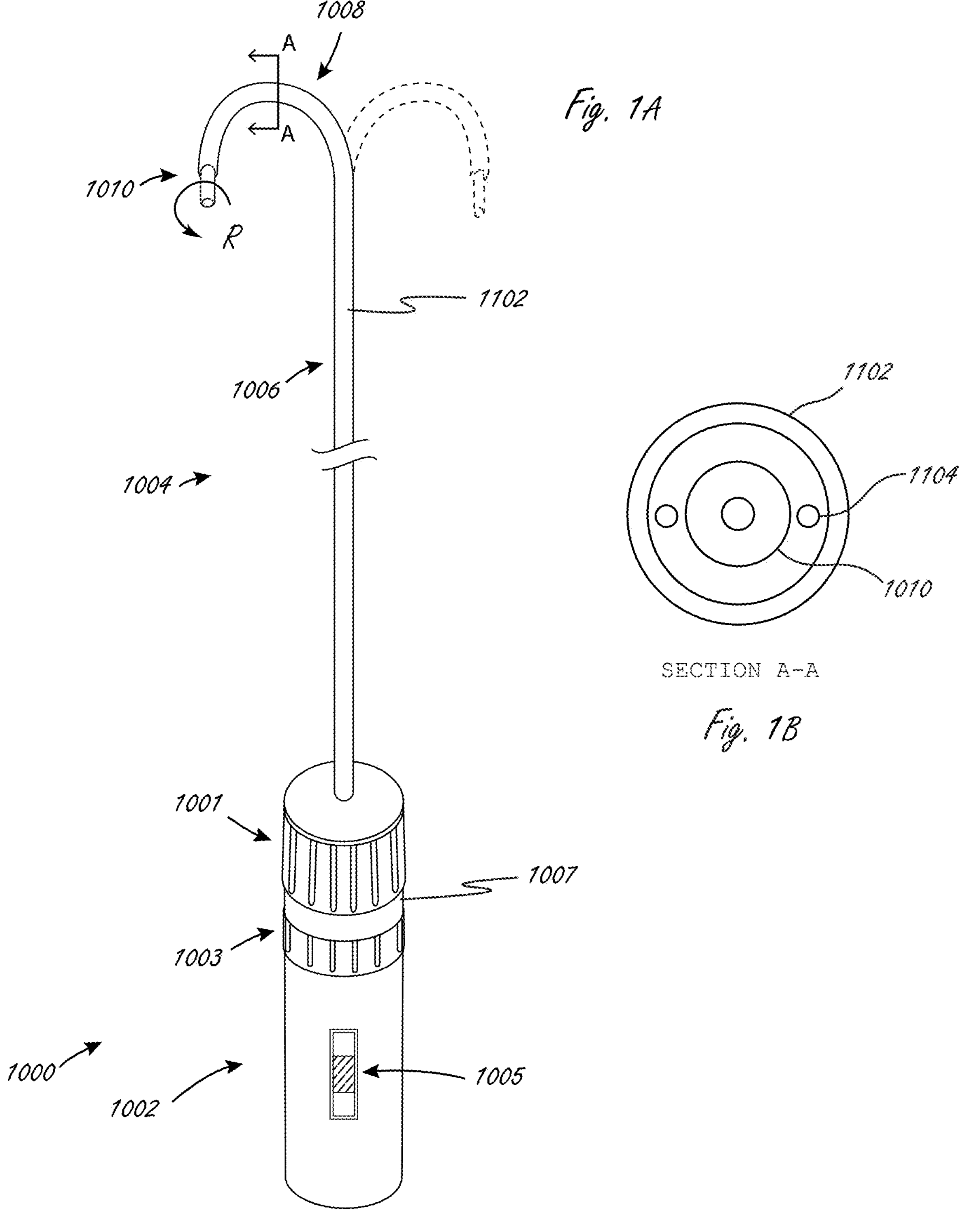
FIG. 1A illustrates an exemplary embodiment of a system that includes steering and a medical device.
FIG. 1B illustrates a cross section A-A of the steering and device portion of the medical device of FIG. 1A.

FIG. 1A illustrates an exemplary embodiment of a system that integrates steering and a medical device. System 1000 includes handle assembly 1002 and steering and medical device portion 1004. Steering and medical device portion 1004 includes a proximal portion 1006 and steerable portion 1008. The system is adapted so that handle assembly 1002 can be actuated to cause steering of the steerable portion 1008, and optionally can be further actuated to cause movement of medical device 1010 relative to steering and medical device portion 1004. In this exemplary embodiment, handle assembly 1002 includes first actuator 1001, second actuator 1003, and third actuator 1005. First actuator 1001 is adapted to be actuated (in this example rotated) relative to handle body 1007 to cause the steering of steerable portion 1008, and specifically steering outer sheath 1102. Steerable portion 1008 in this embodiment can be steered, or bent, into the configuration shown in FIG. 1A in solid lines, and can also be steered into the configuration shown in dashed lines, or anywhere in between, and in some embodiments the opposite steering function is limited to simply straightening the shaft from an initial bent configuration, such as the solid line bent configuration in FIG. 1A. The term "steer" in this disclosure means to deflect or bend, optionally via actuation of at least one pull wire, but in some instances the term can include shaft rotation (torqueing) and axial movement. The term "pull wire" herein refers to any element that may transmit a tensile force from the proximal end of the device to the distal end region. Pull wires may be comprised of metal wire such as stainless steel or nickel titanium, either solid or stranded/braided, or it may be comprised of a polymer such as aramid fiber (Kevlar®), polyethylene, ptfe, eptfe, etc., preferably stranded/braided, but also in monofilament form. In a preferred embodiment, the pull wire is constructed from an aramid fiber bundle having four 50 denier multifilament (approximately 25 filaments) threads braided together at a high picks per inch. The wire cross-sectional diameter is typically in the 0.005"–0.012" range, more preferably 0.008"-0.010", although braided or stranded wire may flatten or ovalize in the device lumen. The preferred construction embodiments are believed to provide optimized strength and wear resistance for the size necessary to keep the shaft diameters to a minimum. Optional second actuator 1003 is adapted to be actuated relative to handle body 1007 (in this example rotated) to cause rotation of medical tool 1010 relative to shaft 1102 (labeled as rotation movement "R"), and optional actuator 1005 is adapted to be actuated relative to handle body 1007 (in this example axially) to cause axial (distal-proximal) movement of medical device 1010 relative the outer sheath 1102. Proximal portion 1006 is not configured to bend significantly when steerable portion 1008 is steered (bent/deflected), although the proximal portion may flex and bend to conform to the anatomy within which it is used. In many embodiments, this is accomplished by constructing the steerable portion 1008 from a softer or less rigid material and/or composite construction than the proximal portion 1006.

The embodiment shown in FIG. 1A is an example of an apparatus that includes an integrated handle assembly that is in operable communication with both a steerable outer shaft and an inner medical tool. The handle assembly is integrated in that it is assembled and constructed to be in operable communication with the outer shaft and the inner medical tool prior to packaging and use. "Integrated" as that term is used in the context of an integrated handle assembly refers to a handle assembly in which at least one part of the handle assembly has to be broken or taken apart before the medical tool can be removed from within the outer shaft.

FIG. 1B illustrates an exemplary cross section A-A (shown in FIG. 1A) of the steering and device portion 1004, and specifically in the steerable portion 1008. In this embodiment medical device 1010 is sized and configured to be disposed within a steerable sheath. The steerable sheath includes an outer shaft 1102 and a set of pull wires 1104, which are axially fixed in a distal region of steerable portion 1008.

The medical tool in FIGS. 1A and 1B can be, for example, any medical tool herein, such as an ultrasound tool. When "ultrasound probe" is used herein, it generally refers to an elongate tool that includes at least one ultrasound transducer and one or more conductive elements that electrically connect the at least one ultrasound transducer to a proximal region of the elongate tool. A proximal region of the ultrasound probe includes, or is modified to include, at least one proximal contact, which is in electrical communication with the at least one ultrasound transducer, and which can be put into electrical communication with, optionally via attachment to, an electrical contact on another device, cable, or connector.

Figure 2:
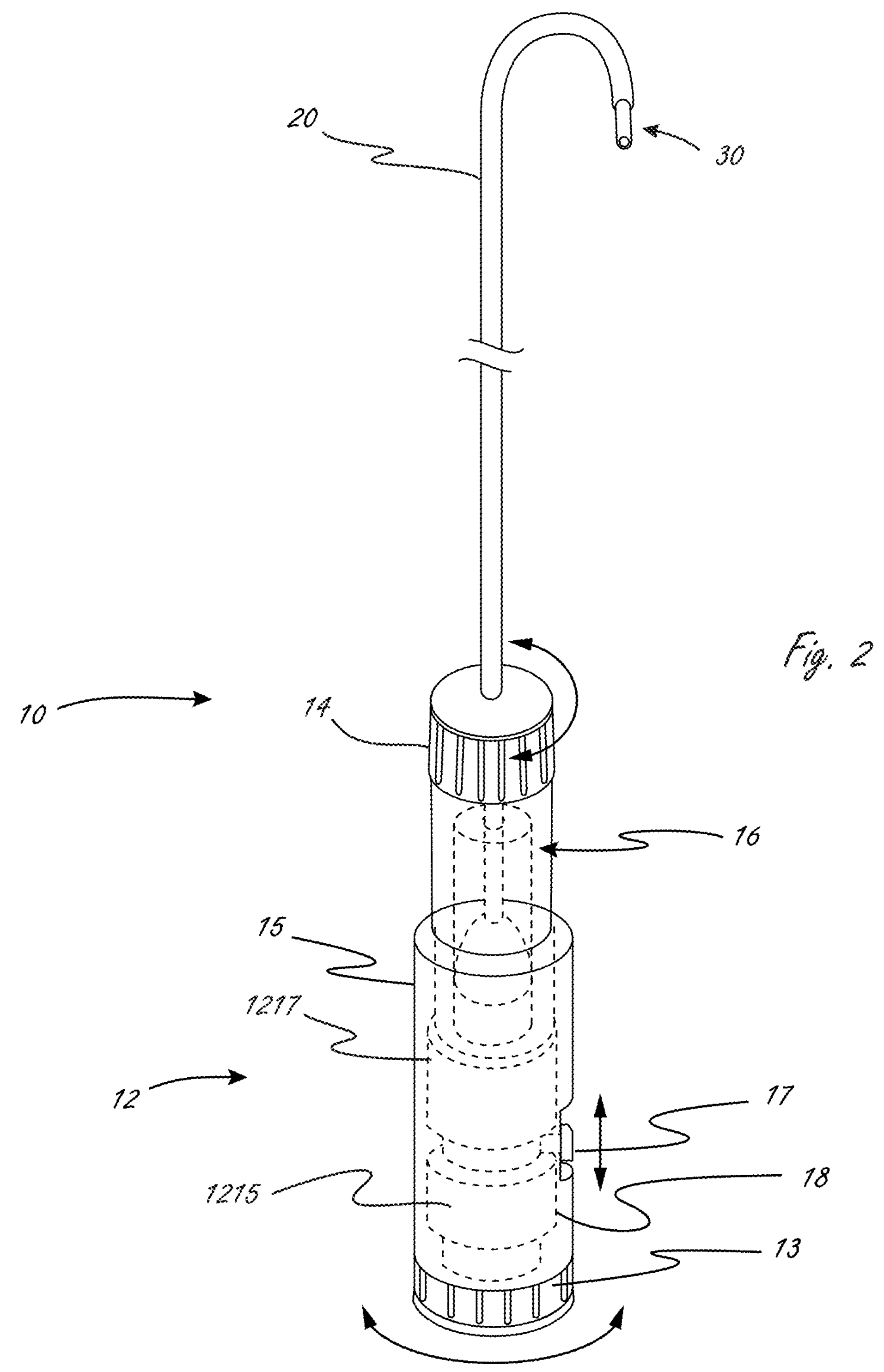
FIG. 2 illustrates an exemplary system that includes a handle assembly with a plurality of actuators, a steerable sheath and medical tool.

FIG. 2 illustrates an exemplary system 10 that is adapted to function similarly to the system in FIGS. 1A and 1B, and also illustrates exemplary internal components of handle assembly 12 (internal components shown as dashed lines). Handle assembly 12 is integrated and in operable communication with outer steerable shaft 20 and medical tool 30. Handle assembly 12 includes actuator 14 that is adapted to, when actuated relative to handle body 15, cause steering of steerable shaft 20. Actuator 14 is in operable communication with steerable shaft 20 via steering control 16 disposed in handle assembly 12. Medical tool 30 includes a proximal portion 18 disposed within and incorporated into handle assembly 12. Actuator 13 is in operable communication with medical tool 30, and actuation of actuator 13 (in this example rotation) relative to handle body 15, causes rotation of medical tool 30 relative to outer shaft 20 via rotation control 1215. Optional third actuator 17 is also in operable communication with medical tool 30, and is adapted to be actuated, in this embodiment, axially (relative to handle body 15), to cause axial movement of medical tool 30 relative to outer steerable shaft 20 via axial control 1217.

The medical tool in FIG. 2 can be, for example, any medical tool herein, such as an ultrasound tool.

FIGS. 3A-3E represent exemplary embodiments of a distal region of the sheath portion 1208 of steerable sheath 1202 in system 1200. For simplicity, the illustrated cross-sections show only the outer sheath 1208 and not the inner tool 1212. The outer sheath 1208 preferably has a composite construction to improve torque transmission applied to the outside of the shaft from the proximal end, or to resist torque forces applied to it from within the shaft, such as from tool 1212.

As illustrated in FIG. 3Ai-iii, in order to form the composite, multiple braid elements 1250, preferably formed from metal wire (round, pairs of round, or ribbon shaped) and/or multiple fibers (e.g., aramid or nylon), may be braided directly over a thin wall (e.g., 0.0010"±0.0005") lubricious liner tube 1251, such as a PTFE or FEP material. A thermoplastic polymer 1252 (such as Pebax in a range of durometers from 25 D-72 D, or nylon, or other common catheter materials) may be laminated with heat using heat shrink tubing (such as FEP) to reflow the polymer over the braid elements 1250 and liner tube 1251 to form a uniform member. The thermoplastic polymer 1252 may also have radiopaque compounds that include materials such as bismuth, barium sulfate, or tungsten in order that the tip of the sheath be visible to the user under fluoroscopy. In the embodiment of FIG. 3Ai-iii, the pull wire 1104 is preferably parallel to the central access in the steerable (deflectable) portion 1222 of the sheath and also preferably provided in a lumen 1253 created within the wall of the steerable sheath 1208. This lumen may be created during the thermoplastic polymer tubing extrusion process or during a shaft heat lamination fusing process with the aid of a removable mandrel. The pull wire lumen 1253 may further be created by incorporating a pull wire tube 1254, preferably temporarily supported by a removable mandrel, within the wall.

The removable mandrel may also be placed alongside the pull line 1104 or 1104' during the fusing process, resulting in a somewhat ovalized lumen 1253 within which a fiber pull wire may be allowed to flatten into, allowing space for free movement of the pull wire. The tube 1254 may include PTFE, FEP, polyimide, or another material which maintains its wall integrity during a heat lamination process up to approximately 500° F. The tube is preferably surrounded and supported by the thermoplastic polymer 1252 which is preferably heat laminated against the tube. In another embodiment, the pull wire lumen, preferably comprising the pull wire tube, is incorporated within the weave of the braid elements 1250. For example, braid elements 1250 running in one direction would pass under the pull wire lumen, while those running in the opposite direction would pass over the pull wire lumen. The braid reinforcement provides a more dimensionally stable lumen during catheter manipulations and also helps assure the straightness of the lumen as needed. Proximal to the steerable portion, the pull wire may continue proximally parallel to the central axis on the same side of the outer sheath 1208, such as is illustrated in FIG. 3Ai-iii. In this embodiment and others that follow, an additional pull wire 1104' within an additional pull wire lumen routed within the wall of sheath 1208, up through the steerable portion 1222, may be required to straighten the steerable portion of the device. This straightening pull wire 1104' is preferably routed within steerable portion 1222 on the side opposite from the pull wire(s) 1104 used for steering (deflection) in the steerable portion 1222. In another embodiment, not shown, two lumens and two straightening pull wires 1104' could be used, essentially mirroring the paired 1104 pull wire configuration. These straightening wires could also be constructed to allow deflection in the opposite direction by tensioning a greater distance (beyond just straightening) within the handle.

Figure 3B:
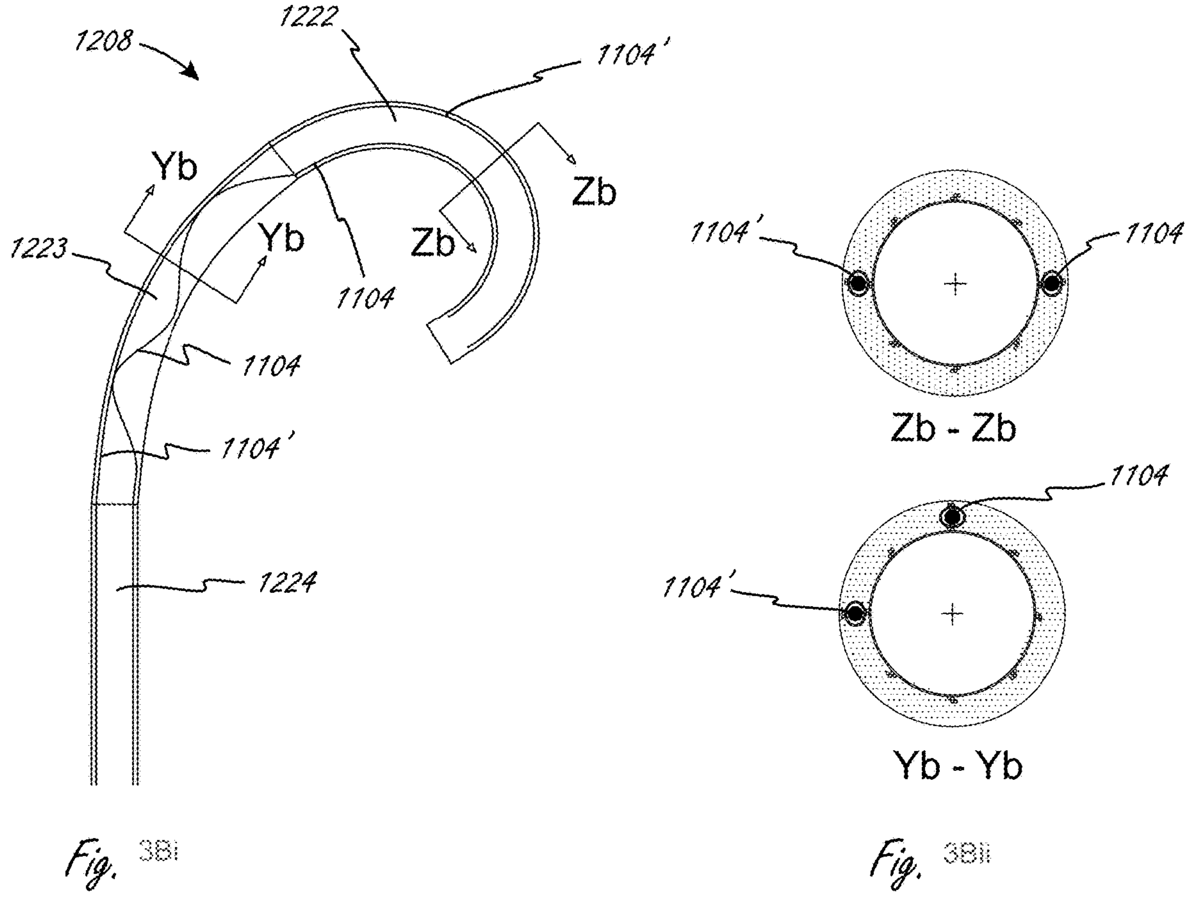
FIGS. 3Bi and 3Bii illustrate an exemplary steerable shaft with pull wires.
Figure 3C:
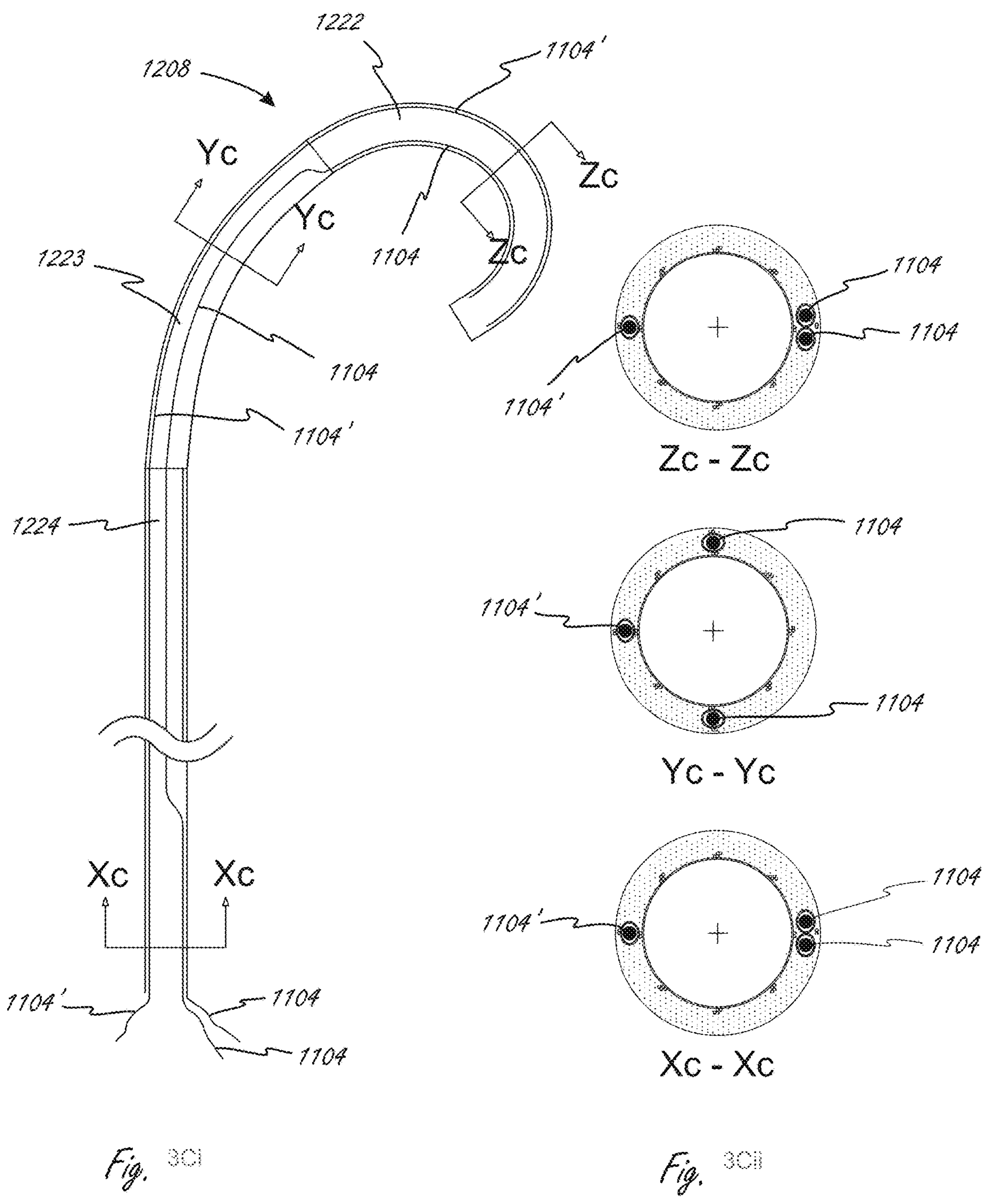
FIGS. 3Ci and 3Cii illustrate an exemplary steerable shaft with pull wires.
Figure 3E:
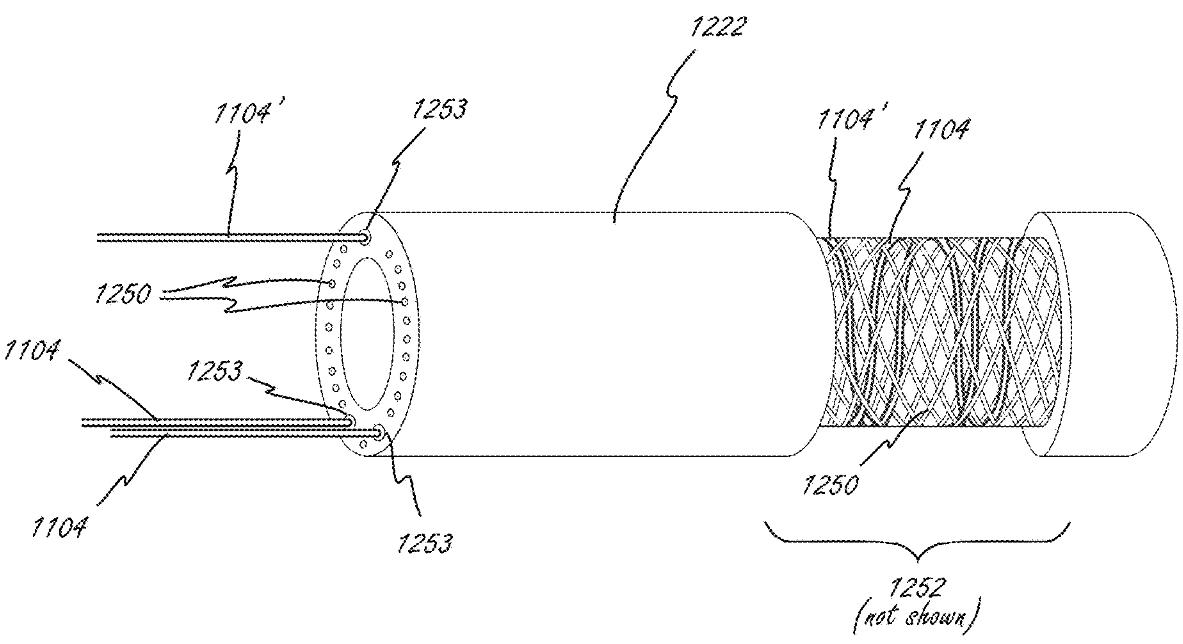
FIG. 3E illustrates an exemplary steerable shaft with one or more pull wires circumferentially interwoven into braid wires of the shaft.

During use, a portion 1223 of the distal catheter just proximal to the steerable (deflectable) portion 1222 may be forced to conform to a curve based on the constraints of the anatomy in which it is used. For a specific embodiment where the device is advanced into the heart chambers from a groin access, the portion 1223 forced into a curve is expected to range from 5 to 25 cm in length. During rotation of the sheath shaft 1208 from the proximal end, torque is transmitted through this distal curved region 1223 to the catheter tip. A non-uniform cross section and/or tension of the device in this region 1223 may induce a tendency for the shaft to build up and suddenly release torque, causing a "whip" or sudden jerk in rotation as it is torqued. To minimize the potential for whip, it is optional to distribute the pull wire tension and construction material around the surface of the curved region 1223. In one embodiment, such as is illustrated in FIG. 3Bi-iii, the pull wire 1104 may spiral around the central axis of the sheath in at least the curved region 1223 proximal to portion 1222. The pull wire of this embodiment may make a full circumferential wrap over approximately 10 cm of length, with this value ranging 5-15 cm. The spiral may only need to be present in the curved region 1223, continuing straight proximally thereafter through proximal portion 1224 (similar to 1006), which may minimize the friction in the pull wire lumen and the associated pull wire force required to steer (deflect) the steerable portion 1222. The spiral may also make a minimum of one turn before continuing straight, or spiral the full length of the shaft. In another embodiment to minimize whip, it may only be necessary to distribute the pull wire tension to opposite sides of the shaft. As illustrated in FIG. 3Ci-ii, deflection of the steerable section 1222 is accomplished with two parallel pull wires 1104 positioned adjacent one another on the same side of the sheath 1208. In the curved region 1223 and proximal portion 1224 (similar to 1006) proximal to the steerable section 1222, the pull wires are routed to opposite sides of the shaft, each 90° from the position in the steerable section 1222, to distribute the tension more evenly. While it is preferable to actuate the two parallel pull wires at the same time with equal force with the handle actuator, in other embodiments, a differential in force could be applied to steer the tip to one side or the other of the plane formed when the two are actuated with equal force. In other embodiments, any plurality of pull wires could be routed in the same configuration as illustrated in FIGS. 3B or FIG. 3C, with the multiple proximal pull wires distributed uniformly around the shaft circumference. Also, as illustrated in FIG. 3Ci-ii, the pull wires 1104 may be routed proximally along the opposite sides of the shaft for most of the shaft proximal portion 1124 length, but preferably brought back together adjacent one another near the proximal end portion of the shaft to allow the wires to exit the same side of the proximal shaft together to facilitate them being secured together to a handle component for simultaneous actuation tension.

FIGS. 3Di-iv illustrate another embodiment of the distal region of catheter with construction similar to that previously described, but instead configured to provide a distal steerable portion 1222 which can be deflected into two different directions. As illustrated, a two pairs of pull wires 1105/1107 and 1106/1108 are along the proximal shaft region 1224 and curved region 1223. This is similar to FIG. 3Ai-iii, except that the wires are paired on each side of the shaft. The routing could also be spiraled as in FIG. 3Bi-ii, or other configurations discussed. Within distal steerable portion 1222, the wires are routed 90° from the proximal portions, although other angles are contemplated. At a junction 1225 within 1222 one or more of the pull wires (e.g., 1105 and 1107) may be terminated and anchored to the shaft, with the remaining pull wires (e.g., 1106 and 1108) continuing to a more distal tip location 1226 where they are anchored. This configuration allows independent actuation of pull wires terminated at 1225 and 1226 such that different shapes may be created during actuation. FIG. 3Dii shows both lines 1107 and 1108 tensioned to create a variable curve in the same direction. FIG. 3Diii shows lines 1107 and 1106 tensioned to create an "S" curve. Other configurations are also possible.

The pull wires (such as 1104 and 1104') must be terminated at their distal end in a manner that reliably affixes them to the wall of the distal steerable shaft portion 1222, such that they do not break or pull free under repeated applications of tension. In a preferred embodiment, shown in FIG. 3E, the pull wires 1104 and 1104', upon exiting the distal pull wire lumen 1253, are circumferentially interwoven into the braid wires 1250 of the distal shaft 1222 (shown without the thermoplastic polymer 1252). One or more of the pull wires 1104 or 1104' may also be additionally or instead wrapped and/or tied around the outside of the braid wires 1250 for additional securing. The braid wires 1250 may be then trimmed distal to the securing point, with the interwoven and/or wrapped pull wires preventing the braid wires from expanding and/or unraveling. Additional adhesives such as UV cured or cyanoacrylates may also be used to secure the pull wires to the braid wires. The weave and/or wrap of the pull wires and braid wires is then laminated with a thermoplastic polymer which melts within the space around the wires and cools to secure them in place. The thermoplastic polymer may also have radiopaque compounds that include materials such as bismuth, barium sulfate, or tungsten in order that the tip of the sheath be visible to the user under fluoroscopy.

In additional embodiments, the tool 1212 may also or alternatively be constructed with one or more pull wires to deflect the tip in a manner similar to any of the previous embodiments described for the outer sheath 1208. In addition to routing the pull wires within the wall of the tubular member of the tool 1212, the pull wires could be routed next to the conductors inside the lumen of the tubular element 1212. Actuation of the pull wires could be from an actuator located in the proximal handle 1206. The distal shaft of tool 1212 may also be formed into a particular shape (e.g., an arc) such that it bends into the shape as it exits the tip of the steerable portion 1222 of outer sheath 1208. The stiffness of the distal shaft of tool 1212 is such that it does not substantially deform outer sheath 1208 while inside, but upon exiting is allowed to bend. The shape may be set by any one or combination of the following means: heat setting the polymeric material, using a moveable or fixed shaped stylet within the inner lumen of shaft 1212 or within a lumen within the wall of shaft 1212. Such a stylet could be round, oval, or rectangular in cross section, and be formed of stainless steel, nitinol, or a rigid polymer such as PEEK, Vestamid, or similar. The outer steerable sheath could alternatively be made to bend with a similar method as above, with or without additional pull wire deflection, and with or without additional shape or deflection of the distal portion of tool shaft 1212.

One aspect of the disclosure includes methods of disassociating at least a portion of the system from other components, optionally as part of a reposing process. In some embodiments the medical tool includes one or more electrical contacts that are coupled to other electrical contacts, which are in electrical communication with an energy console, and examples of consoles are known in the ultrasound art.

Figures 4, 5, 6A, 6B:
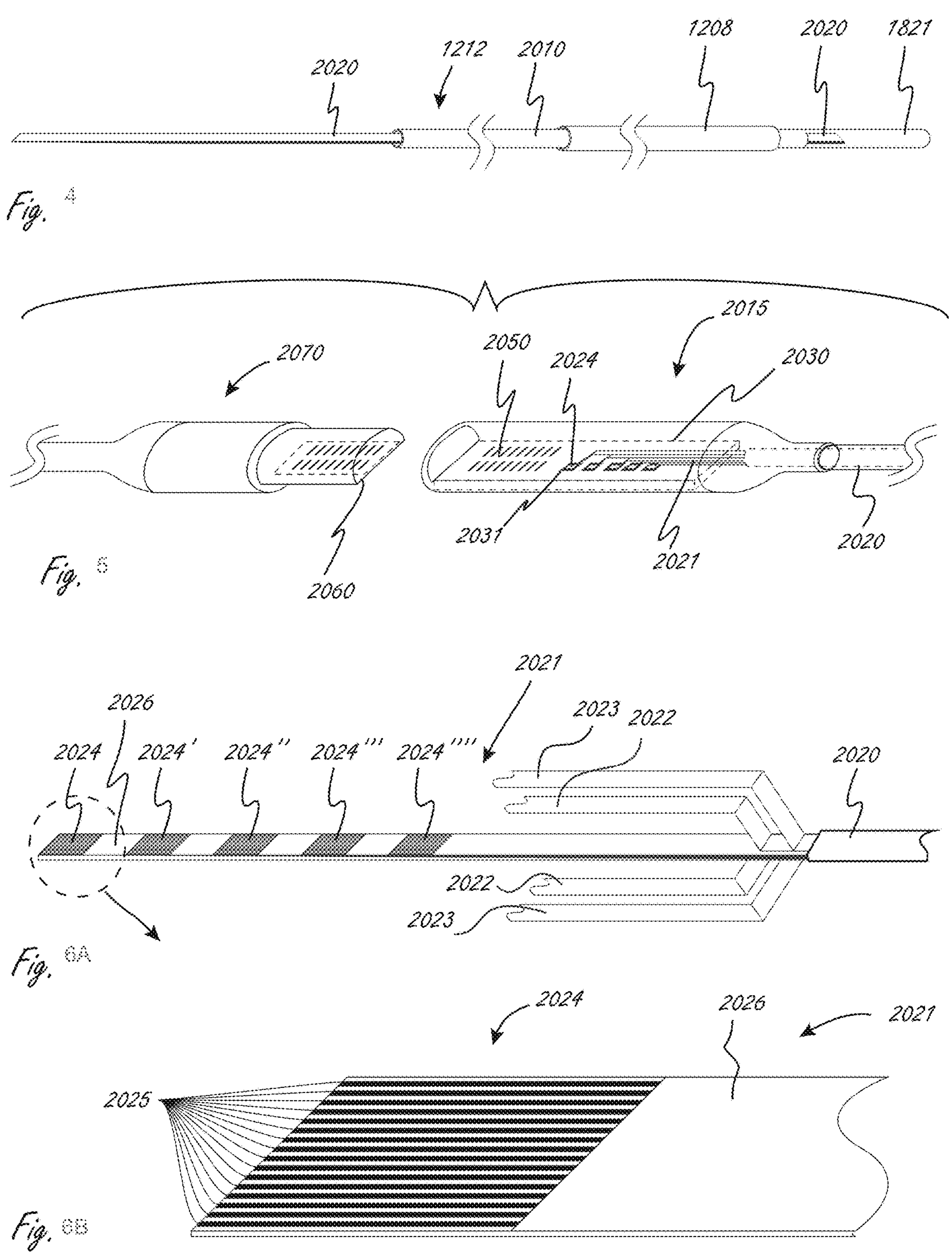
FIG. 4 illustrates an exemplary portion of an exemplary system that includes a bundle.
FIG. 5 illustrates an exemplary proximal end of a medical tool, the tool including a conductor bundle that extends into a proximal connector within which is housed a printed circuit board (PCB).
FIG. 6A illustrates a portion of an exemplary medical tool that includes a flexible circuit strip.
FIG. 6B illustrates an exemplary proximal portion of a strip.

FIG. 4 illustrates merely a portion of an exemplary medical tool, such as an ultrasound probe, that can be electrically coupled directly or indirectly to an energy console, such as an ultrasound console.

Reposing the device can involve disconnection of one or more proximal electrical contacts and moving the tool portion distally out of the distal end of the sheath portion. In this embodiment tool portion 1212 comprises at least a tool outer sheath or member 2010, distal working end 1821 (which can include at least one ultrasound transducer), and conductor bundle 2020. The conductor bundle 2020 extends from the distal working end 1821, through the tool outer member 2010 to a proximal connector (the connector and handle mechanism are not shown in FIG. 18 for clarity). In some embodiments the medical tool is used for ultrasound imaging, optionally where the distal working end 1821 comprises a two-dimensional (2D) array of piezo electric components mounted on an ASIC (application specific integrated circuit).

FIG. 5 illustrates a merely exemplary proximal end of a medical device (the medical device is shown on the right), and in this embodiment the medical device is an ultrasound probe. The proximal end 2015 of the medical device is adapted to be electrically coupled to connector cable 270, which is directly or adapted to be indirectly electrically coupled to an energy console, such as an ultrasound energy console. As illustrated in FIG. 5, flexible conductor bundle 2020 extends from a distal region of the medical tool (distal region not shown) into a proximal connector 2015 within which is housed a rigid or flexible printed circuit board ("PCB") 2030. The connector bundle 2020 includes a plurality of contacts 2024 (examples of which are described below) that are attached to PCB board contacts 2031. Each individual trace from each contact 2031 is linked to individual exposed contacts 2050 on another portion, optionally more proximal, of the PCB. The individual PCB traces may also pass through other useful circuitry on the PCB. The exposed contacts 2050 are configured for a mechanical mating for electrical conduction to similar contacts 2060 on mating connector cable 2070, similar in concept to the proximal tool connector 1990 described previously, which links the tool 1204 to a user-interface console. Proximal connector 2015 can be incorporated into any of the systems, handles, steerable sheaths, medical tools, etc., herein.

"Conductor bundle" as that term is used herein may be interchangeably used with "flexible conductor bundle" unless indicated to the contrary herein.

FIGS. 6A and 6B illustrate an exemplary conductor strip (also referred to herein as a flexible circuit strip) 2021 that can be included in any of the conductor bundles herein. The embodiment in FIGS. 6A and 6B is an example of a conductor strip that can be included in bundle 2020 from FIGS. 4 and 5. The embodiment in FIGS. 6A and 6B can be incorporated into any other system herein.

Figure 6C:
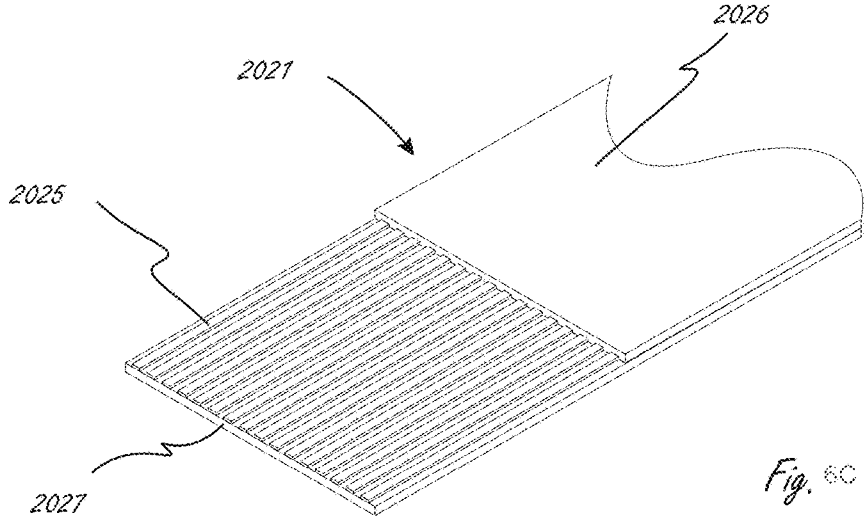
FIG. 6C illustrates a detailed view of an exemplary proximal portion of a strip.
Figures 6D, 6E, 6F, 6G:
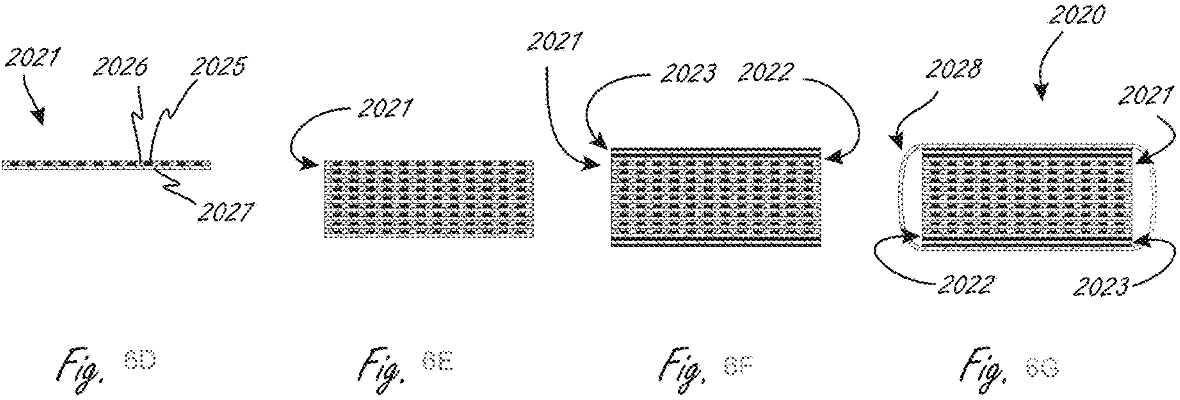
FIG. 6D illustrates an end view of an exemplary flex strip.
FIG. 6E illustrates an exemplary stack of flex strips.
FIG. 6F illustrates an exemplary stack of flex strips and ground and shield strips.
FIG. 6G illustrates an exemplary bundle including a tubing material around a stack of strips and shield and ground strips.

As shown in FIGS. 6A, 6B and 6G, conductor bundle 2020 comprises a plurality of flex circuit strips, including multi-trace strips 2021, as well as conductive strips for grounding 2022 and shielding 2023 (only a portion of which are shown). Each multi-trace strip comprises a plurality of conductive traces 2025, which can be seen clearly in FIGS. 6B, 6C and 6D. The number traces 2025 in FIGS. 6D-G is twelve, and the number of traces in FIGS. 6A-6C is sixteen, and they are both exemplary as to the number of traces 2025 that can be used. Each strip 2021 can be approximately 0.072" wide and 0.0022" thick, and can optionally comprise sixteen 0.0022" wide×about 0.0007" thick conductive (e.g., copper) traces, each spaced approximately 0.0022" apart. The traces are disposed on an insulating substrate layer 2027, such as a polyimide substrate, and the traces can be at least partly covered by a cover layer 2026, such as a photoimageable film cover ("PIC") layer or other dry film solder mask (DFSM) or other similar material. The cover layer generally extends along most of the bundle, except at discrete locations in proximal and distal regions for electrical coupling. In other embodiments, the strip 2021 is approximately 0.055" wide and comprises twelve conductive traces (see FIGS. 6D-G). In other embodiments, the strip 2021 is approximately 0.037" wide and comprises eight copper conductive traces. The outer strips 2022 and 2023 used for grounding and shielding may have a similar construction and dimension except they can comprise a single full width strip of copper. As optimized for a 2D piezo array, a stack of approximately seven 16-trace strips 2021 would be required (or nine 12-trace, or fourteen 8-trace), along with one each of strips 2022 and 2023 on each side of the stack of multi-trace strips. FIG. 6E illustrates a portion of an exemplary bundle 2020 with nine strips 2021 stacked together. FIG. 6F illustrates a portion of the bundle that includes nine strips 2021 stacked, as well as ground strip 2022 and shield strip 2023 (only those on top are labeled). The complete bundle may optionally be held together with a, for example without limitation, about 0.001" wall thickness shrink tube, such as the tubing 2028 in FIG. 6G. The flex circuit dimensions and number of traces discussed above are for a particular configuration of a piezo-electric array (and/or an ASIC controller thereof) and may be varied depending on how the number and size of array elements are optimized for the particular application.

The proximal end of each flex circuit strip has the conductive material (e.g., gold-plated copper) exposed over a length of approximately, for example, 3 mm through removal of the cover layer 2026 at location 2024. Location 2024, and other exposed locations described herein, is generally referred to as a "contact." It is understood that when used in this context, the contact actually includes a plurality of separated conductive traces (such as shown in region location), each of which is adapted to be in electrical communication with its own corresponding conductive element. "Contact" is therefore not limited to mean only a single electrical connection between two conductive elements. While FIG. 6A shows a plurality of exposed regions 2024, the embodiment in FIG. 6A will first be described herein as if there is only one exposed region (i.e., region 2024 at the proximal end). The strip 2021 can be made to create an electrical connection to matching exposed contacts 2031, shown in FIGS. 6A-C, for conductive traces on the PCB 2030. In some embodiments, sixteen individual traces, sized and spaced to match sixteen traces in the multi-trace strip 2021, would be provided within a given contact 2031. An ACF (anisotropic conductive film), soldering, conductive adhesive, mechanical connection, or any combination of these may be used to achieve a suitable electrical connection (electrical coupling) between the strip traces and the PCB contacts.

Figure 7:
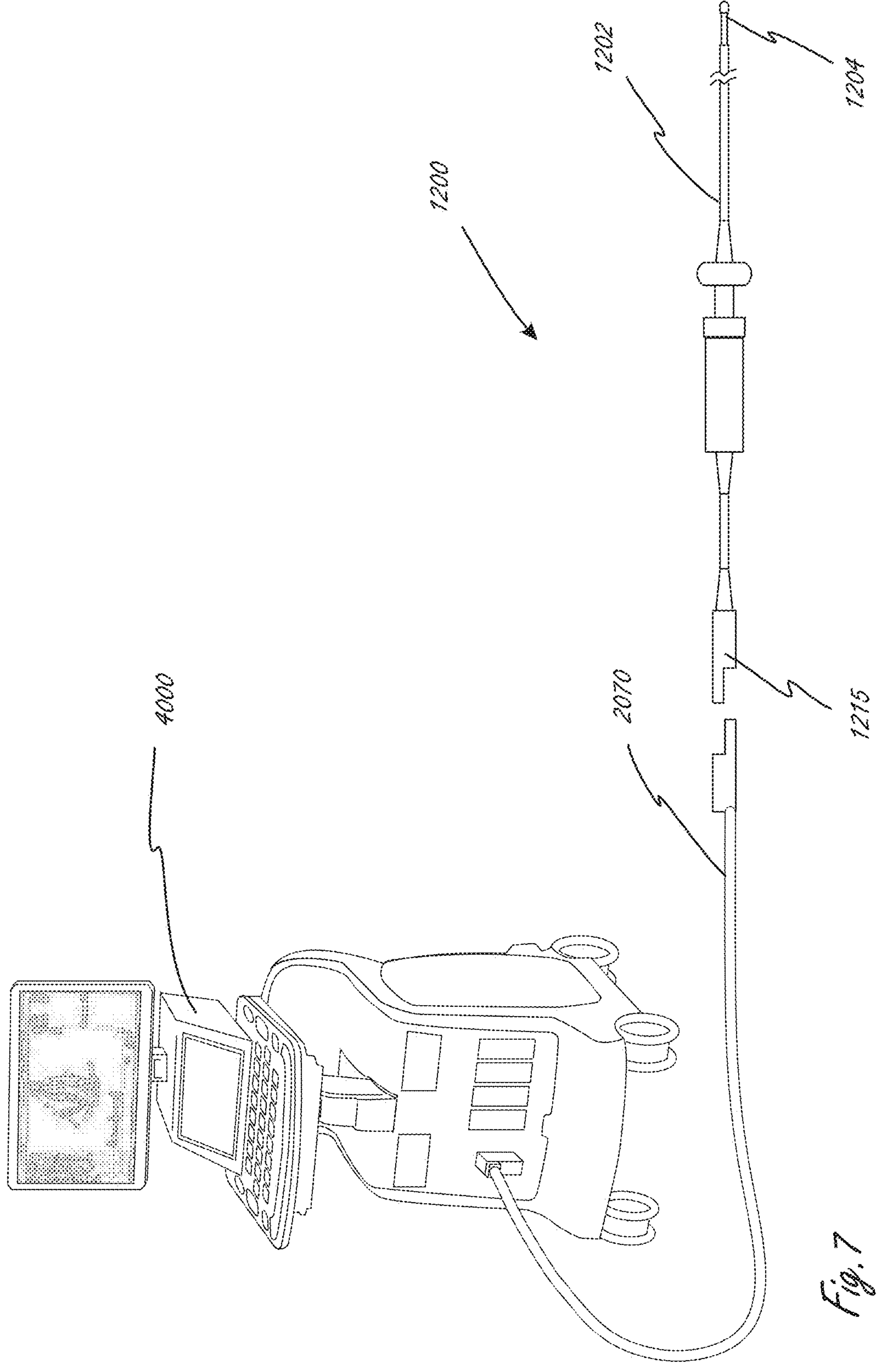
FIG. 7 illustrates an integrated system of the steerable sheath and medical tool wherein the system is connected to a console via a connector cable.

FIG. 7 illustrates the integrated system 1200 of the steerable sheath 1202 and medical tool 1204 wherein the system 1200 is connected to console 4000 via the connector cable 2070. As previously described, such as for FIG. 5, the tool 1204 comprises a proximal connector 2015 which forms a mating connection to cable 2070. As previously described, it is desirable to repose (e.g., reprocess and reuse) the system 1200. It is further desirable to ensure that the system is reposed only by the original manufacturer and not an unaffiliated third-party, and to ensure the device is only reused a specified number of times. To control the reposing process, a crypto-authentication chip (crypto-chip) is incorporated into the tool 1204, preferably on the PCB 2030, although other locations, such as within the steerable handle 1206, or within the tip 3000, are contemplated. The crypto-chip is programmable only by the original manufacturer who controls the authentication keys. The console 4000 to which the system 1200 is connected has a Trusted Platform Module (TPM) which also has the authentication keys. During use of the system 1200, the console 4000 is able to authenticate the system 1200 via the crypto-chip and as desired may read and write information to the chip (e.g., via an EEPROM feature). In any of the scenarios discussed, RFID chips, preferably encrypted, may be used to read and transmit data between the console, connector, and the device.

As used herein, "cleaning" can refer to any type of cleaning, such as without limitation: cleaning an interior of an outer shaft using a flushing system of cleaner and/or disinfectant and optionally mechanical scrubbing with small brushes; mechanical cleaning (e.g., wipes, brushes) an outer portion of an outer shaft and/or outer portion of a medical device shaft (e.g., ultrasound probe) with a cleaner/disinfectant, and optionally submerging the shaft in an ultrasound bath of cleaner/disinfectant for a specified period of time; and optical cleaning methods such as comprising using UV light. "Cleaning" as used here does not refer to a specific cleaning process, but rather refers to the general idea of cleaning an object.

The disclosure herein also includes methods of assembling or reassembling any of the subassemblies or assemblies herein, including any of the subassemblies within any of the handle assemblies herein. For example without limitation, the disclosure here includes methods of spooling one or more pull wires over a bearing surface in a spindle support and then around the spindle.

The methods herein also include manufacturing or constructing any of the individual components of any of the subassemblies or assemblies herein. For example, the disclosure includes methods of manufacturing handle shell components that have particular configurations (e.g., guides, walls, etc.) that can accommodate the internal parts that allow the assemblies or subassemblies herein to function as intended.

Regardless of the reference number with which they are labeled, any of the handle assemblies, medical tools, steerable sheaths, and electrical connections herein can be used together in a system in any combination with each other.

Any of the technology, including ultrasound and steering technology, in any of the following U.S. patent references may be incorporated into any of the medical tools, devices, systems, or methods of use thereof herein, the disclosures of which are incorporated by reference herein: U.S. Pat. Nos. 6,100,626, 6,537,217, 6,559,389, 7,257,051, 7,297,118, 7,331,927, 7,338,450, 7,451,650, 7,451,650, 7,527,591, 7,527,592, 7,569,015, 7,621,028, 7,731,516, 7,740,584, 7,766,833, 7,783,339, 7,791,252, 7,791,252, 7,819,802, 7,824,335, 7,966,058, 8,057,397, 8,096,951, 8,207,652, 8,207,652, 8,213,693, 8,364,242, 8,428,690, 8,451,155, 8,527,032, 8,659,212, 8,721,553, 8,727,993, 8,742,646, 8,742,646, 8,776,335, 8,790,262, 8,933,613, 8,978,216, 8,989,842, 9,055,883, 9,439,625, 9,575,165, 9,639,056, and 20080287783.

Any suitable disclosure above can be incorporated into any of the embodiments below. For example, aspects of devices, systems, and methods of manufacture and use are incorporated herein and can be incorporated into any of the embodiments below unless specifically indicated to the contrary.

Figure 8A:
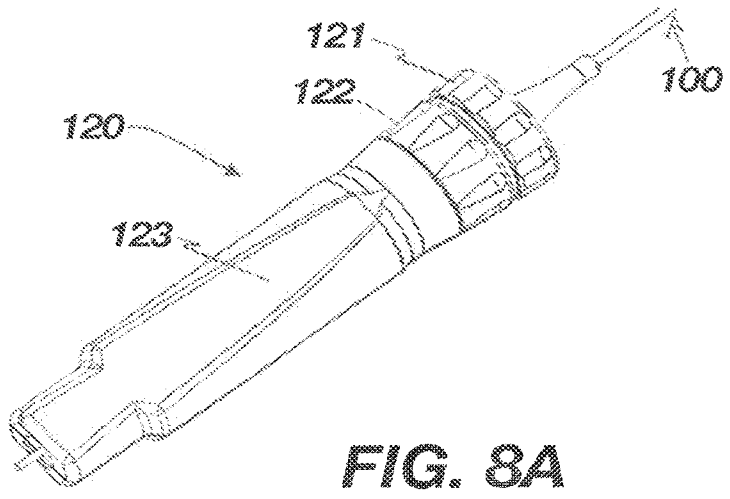
FIGS. 8A and 8B illustrate an exemplary handle assembly that can be used with any of the inner and outer elongate bodies or shafts herein.
Figure 8B:
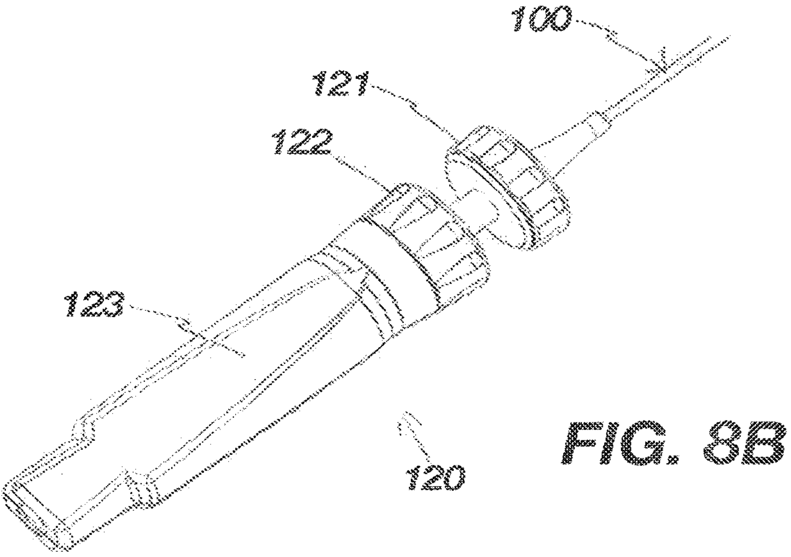

FIGS. 8A and 8B illustrate a merely exemplary handle assembly that may be in operable communication with outer shaft 131 and inner shaft 132. In this exemplary implementation, handle assembly 120 includes handle body 123 that has an outer surface that can be gripped by a user, first actuator 121, and second actuator 122. Actuator 121 can be in operable communication with outer shaft 131, and actuator 122 can be in operable communication with inner shaft 132. Actuator 121 is adapted to be both rotated and moved axially relative to handle body 123 (and relative to second actuator 122). This allows actuator 121 to cause axial movement of the medical tool 103 and rotation of the medical tool 103 relative to a distal end of inner shaft 132. Second actuator 122 is adapted to be actuated (e.g., rotated in this embodiment) relative to handle body 123 to cause deflection of the inner shaft 132. For example, the handle assembly can have internal components that interface with proximal ends of pull wires such that actuation of actuator 122 tensions one or more pull wires to cause deflection of the inner shaft. In this embodiment actuator 121 is distal to actuator 122, but in other designs their relative positions could be reversed. FIG. 8B shows handle assembly 120 after actuator 121 has been advanced distally relative to its position in FIG. 8A. This distal advancement causes outer shaft 131 to be advanced distally, and thus causes the medical tool to be advanced distally. Actuator 121 can similarly be retracted proximally relative to its position in FIG. 8B. Tensioning members described further below are referenced with respect to actuator 121 being retracted proximally.

In other designs, actuator 121 could be in operable communication with an inner shaft and actuator 122 may be in operable communication with an outer shaft.

As described herein, the outer shaft can be moved axially relative to the inner deflectable shaft. The outer shaft may be constructed with sections of materials that vary in stiffness (e.g., durometer) along the length of at least a portion of the outer shaft. For example, a first portion that is distal to a second portion can have a lower durometer than the second portion. Because the outer shaft can be moved axially relative to the deflectable inner shaft, and because the stiffness of the outer shaft can vary along its length, the deflection, including the degree (or amount), of the overall device can be selectively controlled by controlling the axial position of the outer shaft (relative to the inner shaft). Axial movement of the outer shaft can thus selectively control deflection of the device. For example, a user (e.g., physician) can change or control where the bend occurs along the length of the device (measured from the distal end) by axially moving the outer shaft relative to the inner shaft. Additionally, for example, sections of varying stiffness in the outer shaft can allow for more or less deflection depending on the relative position of the outer shaft relative to the deflectable inner shaft. For example, deflecting the inner shaft at a region where the outer shaft has a relatively higher stiffness can result in less deflection than when the inner shaft is deflected at a region where the outer shaft has less stiffness.

FIG. 9C shows exemplary apparatus medical apparatus 130, which includes elongate inner shaft 132 (see FIG. 9A) and elongate outer shaft 131 (see FIG. 9B). Medical apparatus 130 may also be referred to herein as a "catheter," or other medical device that includes at least one elongate shaft.

Figure 9D:
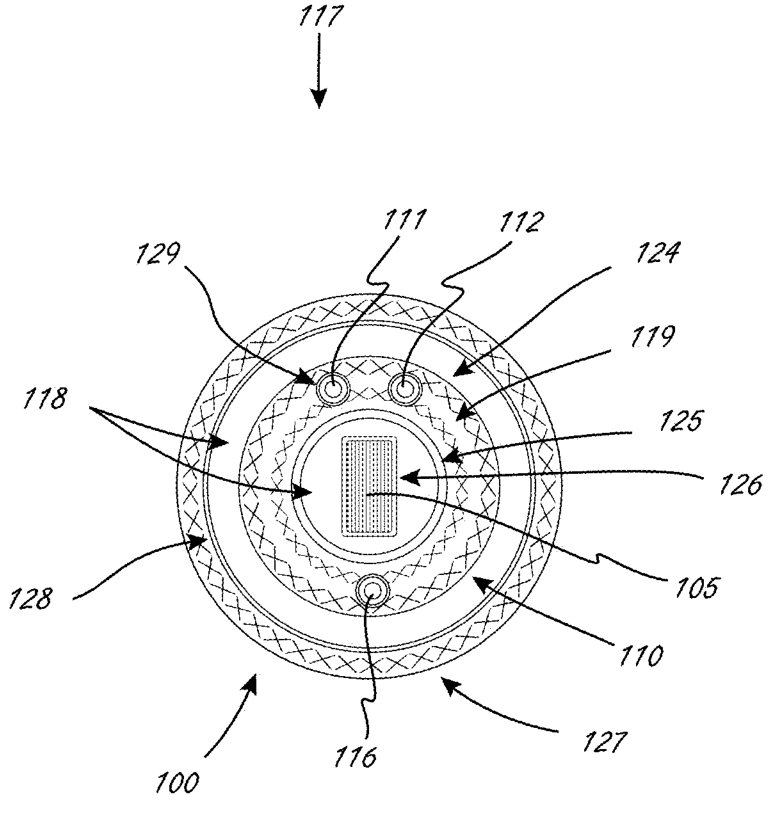
FIG. 9D illustrates a section of the device in the deflectable portion from FIG. 9C.

FIG. 9D illustrates Section A-A shown in the assembly in FIG. 9C, which is a section in the deflectable section of the device. Parts from FIGS. 9A-9C are similarly labeled. As can be seen in FIG. 9D, pull wires 111 and 112 are very near to one another and about 180 degrees away from straightening pull wire 116.

As is also shown in FIG. 9D, elongate inner shaft 132 includes two layers of braided material 119, and the pull wires are, at least at the location of this section, essentially sandwiched between the two layers of braided material. Annular spaces 118 allow freedom of movement and space for optional lubricant. Inner shaft 132 may be made from, for example without limitation, a polymeric material such as Pebax, optionally with a lubricious additive. Inner shaft 132 may include liner 125, such as a PTFE liner. The flexible cable bundle 105 may be surrounded by one or more layers of insulation 126, such as PTFE insulation. Outer shaft 131 may comprise a polymeric material 127, such as Pebax. Outer shaft 131 may also include a radially inner liner 128, such as a PTFE liner. Any of the pullwires (e.g., 111, 112, 116) may be disposed in a lumen with a liner, such as PTFE liner 129.

Medical apparatus 130 (or either of elongate shaft 132 and elongate shaft 131, individually) can be in operable communication with any of the handle assemblies herein, including handle assembly 120 shown in FIGS. 8A and 8B.

FIGS. 10A-10C and FIG. 11 illustrate an additional exemplary handle assembly that can be in operable communication with any of the medical devices, including ultrasound probes, herein. For example, the exemplary handle assembly shown in FIGS. 10A-10C can be coupled to (directly or indirectly) and in operable communication with medical apparatus 130 shown in FIGS. 9A-9D. In a particular embodiment, both elongate outer shaft 131 and elongate inner shaft 132 are coupled to and in operable communication with the handle assembly shown in FIGS. 10A-10C.

Figure 10A:
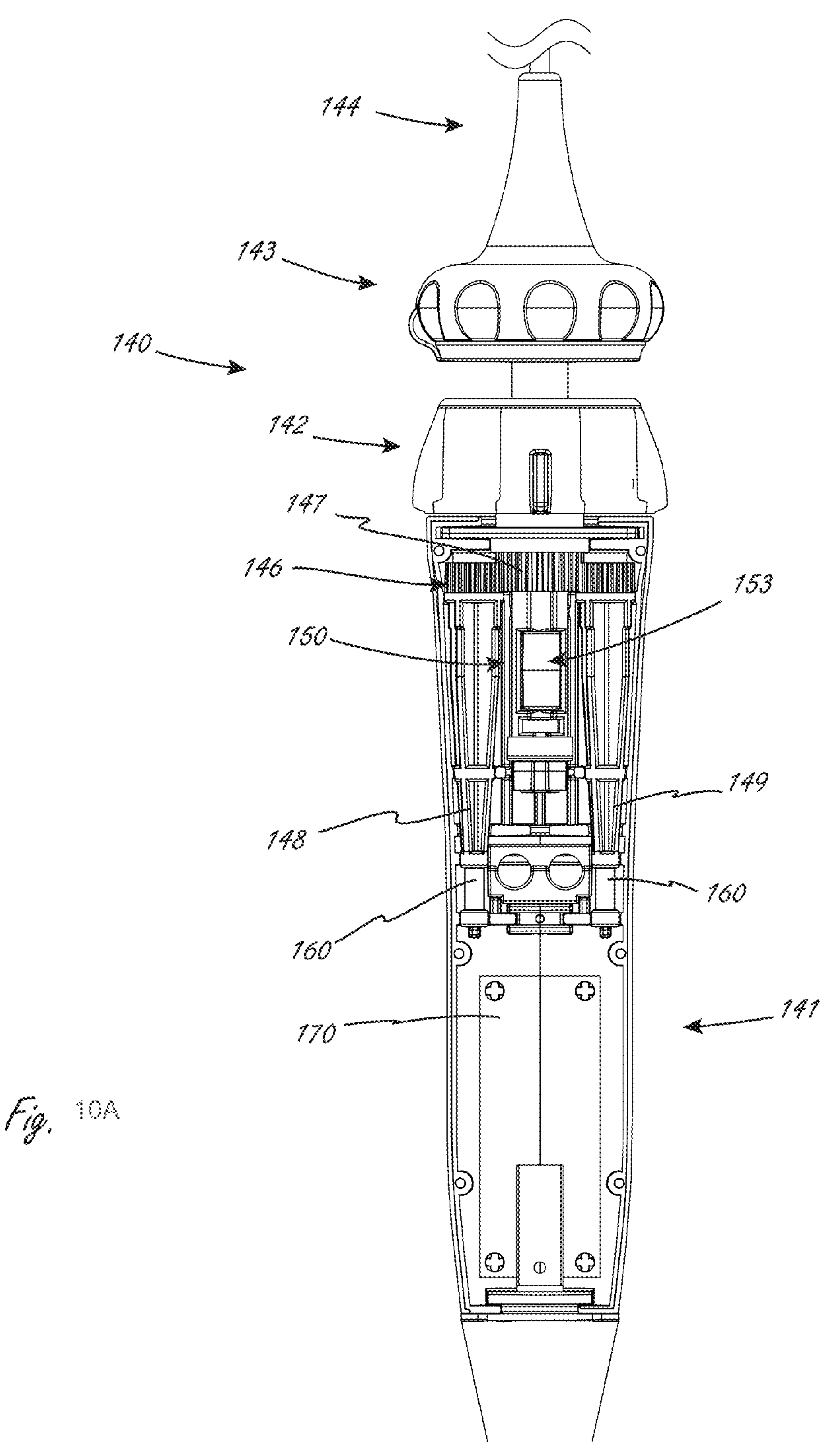
FIG. 10A illustrates a portion of an exemplary handle assembly.
Figure 10B:
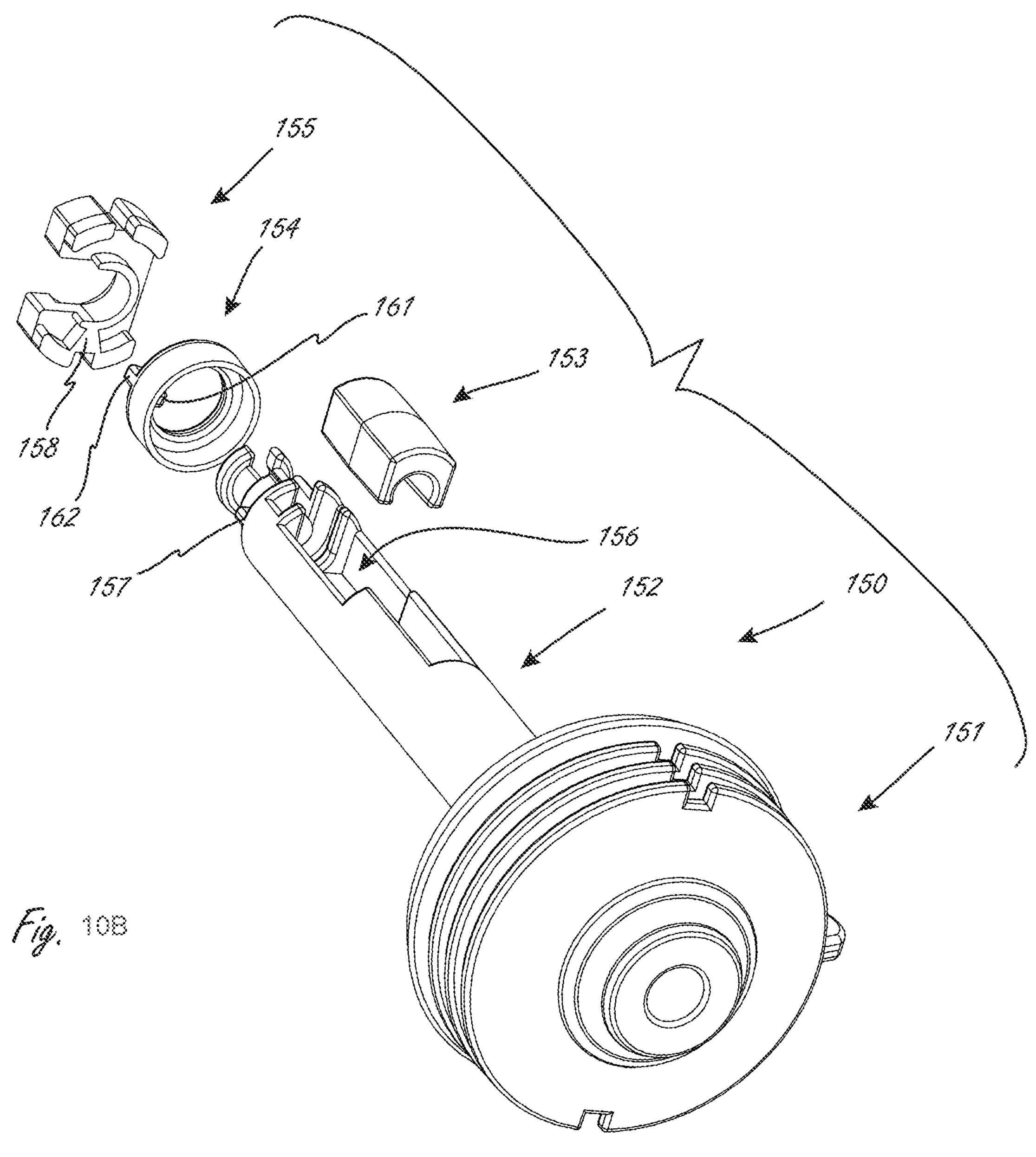
FIG. 10B is an exploded view illustrating an exemplary outer elongate body (or outer shaft) movement subassembly.
Figure 10C:
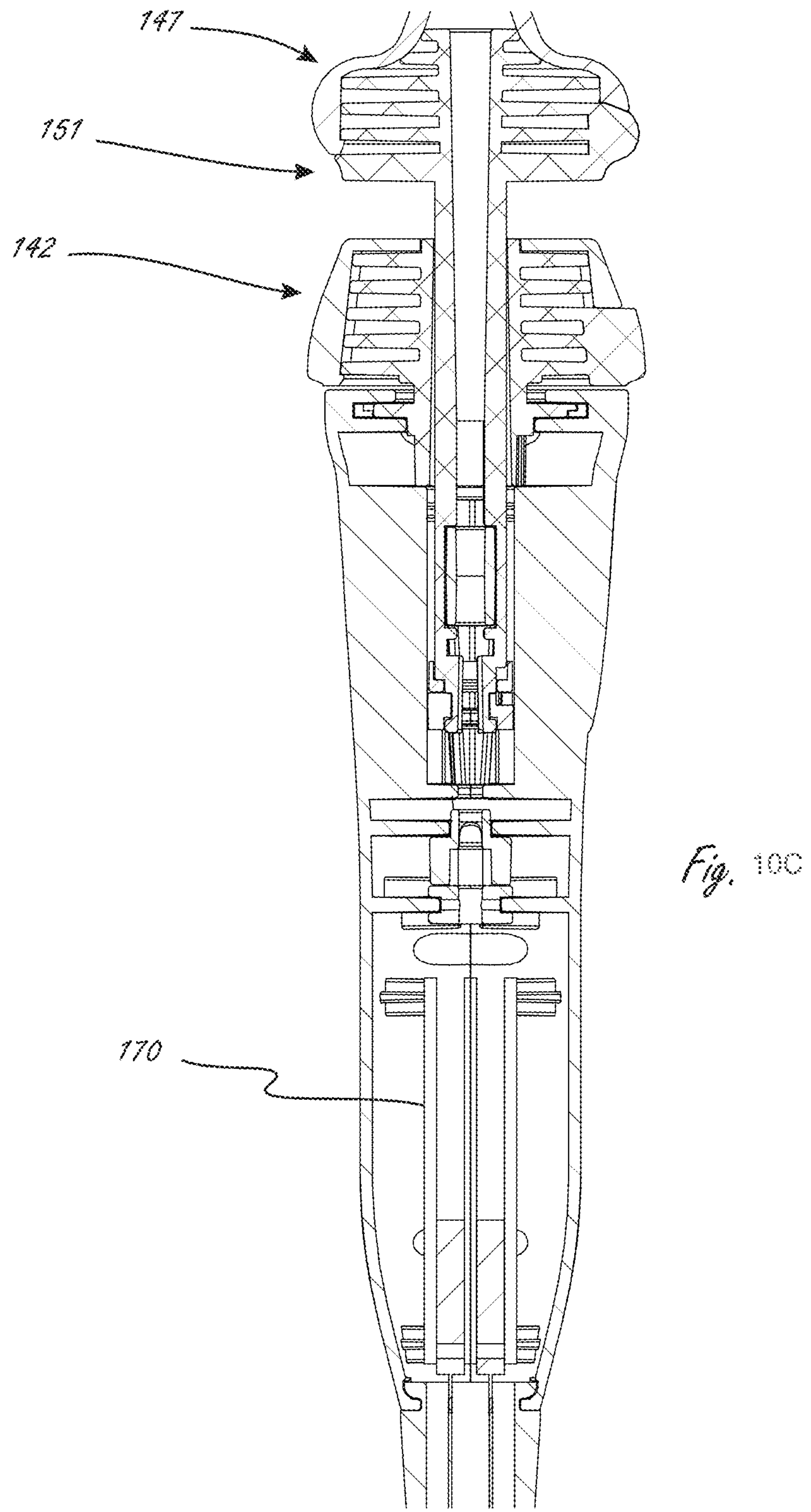
FIG. 10C illustrates a side sectional view of the handle assembly from FIG. 57A.

The handle assembly in FIGS. 10A-10C and FIG. 11 has some similarities to the handle assemblies, the individual components, and subassemblies that are shown in FIGS. 8A and 8BB. Unless indicated to the contrary, concepts, features and methods of use from FIGS. 8A and 8B that can be incorporated into the handle assembly in FIGS. 10A-C are hereby incorporated by reference for all purposes into the disclosure of the handle assembly shown in, and described with respect to, FIGS. 10A-C. Similarly, concepts, features and methods of use that are shown in, and described with respect to, FIGS. 10A-C that can be incorporated into other handle assemblies herein are hereby incorporated by reference for all purposes into the disclosure of any of the handle assemblies set forth herein.

FIG. 10A is side view of handle assembly 140 with a portion of handle body 141 removed so that some internal components of the handle assembly can be seen. Handle assembly 140 includes first actuator 143 and second actuator 142, and in this embodiment first actuator 143 is distal to second actuator 142. First actuator 143 can be both moved axially and rotated relative to the handle body and relative to a second actuator (in this embodiment actuator 142). First actuator 143 is in operable communication with an outer elongate body, such as outer shaft 131 (see FIG. 9B). Axial movement of actuator 143 (distally or proximally) causes axial movement of the outer shaft 131, while rotation of actuator 143 causes rotation of the outer shaft. Second actuator 142 is in operable communication with an inner shaft, such as inner shaft 132 (FIG. 9A). Actuation of second actuator 142, in this embodiment rotation, causes deflection of the inner shaft. In this embodiment a rotatable and axially movable actuator (i.e., first actuator 143) is in operable communication with an outer shaft.

First actuator 143 is coupled to elongate outer shaft movement assembly 150 shown in the exploded view in FIG. 10B, such that movement of first actuator 143 causes movement of assembly 150. Elongate outer shaft movement assembly 150 is similarly coupled to the elongate outer shaft so that movement of first actuator also causes movement of the elongate outer shaft. In this embodiment, the outer elongate shaft is attached to removable part 153 after it is inserted into channel 156. Removable part 153 and channel 156 are configured so that removable part 153 is constrained by at least one inner surface of channel 156 when it is inserted therein. Elongate outer shaft movement assembly 150 also includes a distal head portion 151 that is secured to first actuator. Elongate outer shaft movement assembly 150 also includes a rotation limiting mechanism similar to that which is described herein, which limits the rotation of first actuator 143, and thereby limits the rotation of the outer elongate shaft. Any of the disclosure above related to rotation limiting subassemblies, functionality, and use, is incorporated into this embodiment for all purposes and may be incorporated into this and similar designs. During rotation, part 157 (see FIG. 10B) interacts with part 161, and part 162 interacts with part 158. The physical interactions of these two sets of parts limits rotation to the desired rotation limit, e.g., such as limiting rotation up to 630 degrees of rotation of the outer body (in other embodiments the allowed rotation could be more than 630 degrees, such as up to and including 720 degrees).

If it is desired to clean the outer shaft, for example after use, removable part 153 can be detached from the outer shaft to allow the outer shaft to be removed from the handle assembly and cleaned, before being reinserted and reattached to removable part 153 or a new removable part if part 153 is damaged or broken.

Handle assembly 140 also includes inner shaft deflection assembly 146, which is in operable communication with second actuator 142. Inner shaft deflection assembly 146 includes central gear 147 adapted and configured to rotate when second actuator 142 is rotated. Central gear 147 interfaces first spindle 148 and second spindle 149 via a geared interface, such that rotation of central gear 147 causes rotation of the spindles in the opposite direction. The inner shaft deflection assembly 146, including the spindles, extends further proximally than the elongate outer body movement assembly 150. The inner shaft extends through the outer shaft and extends further proximally than the outer shaft within handle assembly 150. This allows one or more pullwires that are part of the inner shaft to extend radially outward and interface with reels 160.

The lack of interaction between elongate outer shaft movement assembly 150 and elongate inner shaft movement assembly 146 allows for the inner and outer elongate shaft to be independently controlled by first actuator 143 and second actuator 142.

Handle assembly 140 also includes printed circuit board ("PCB") 170 disposed within handle body 141, the PCB being in electrical communication with a cable bundle, such as flexible cable bundle 105 in FIG. 53, or any of the cable bundles herein that are in communication with the medical tool, such as an ultrasound transducer.

Figure 11:
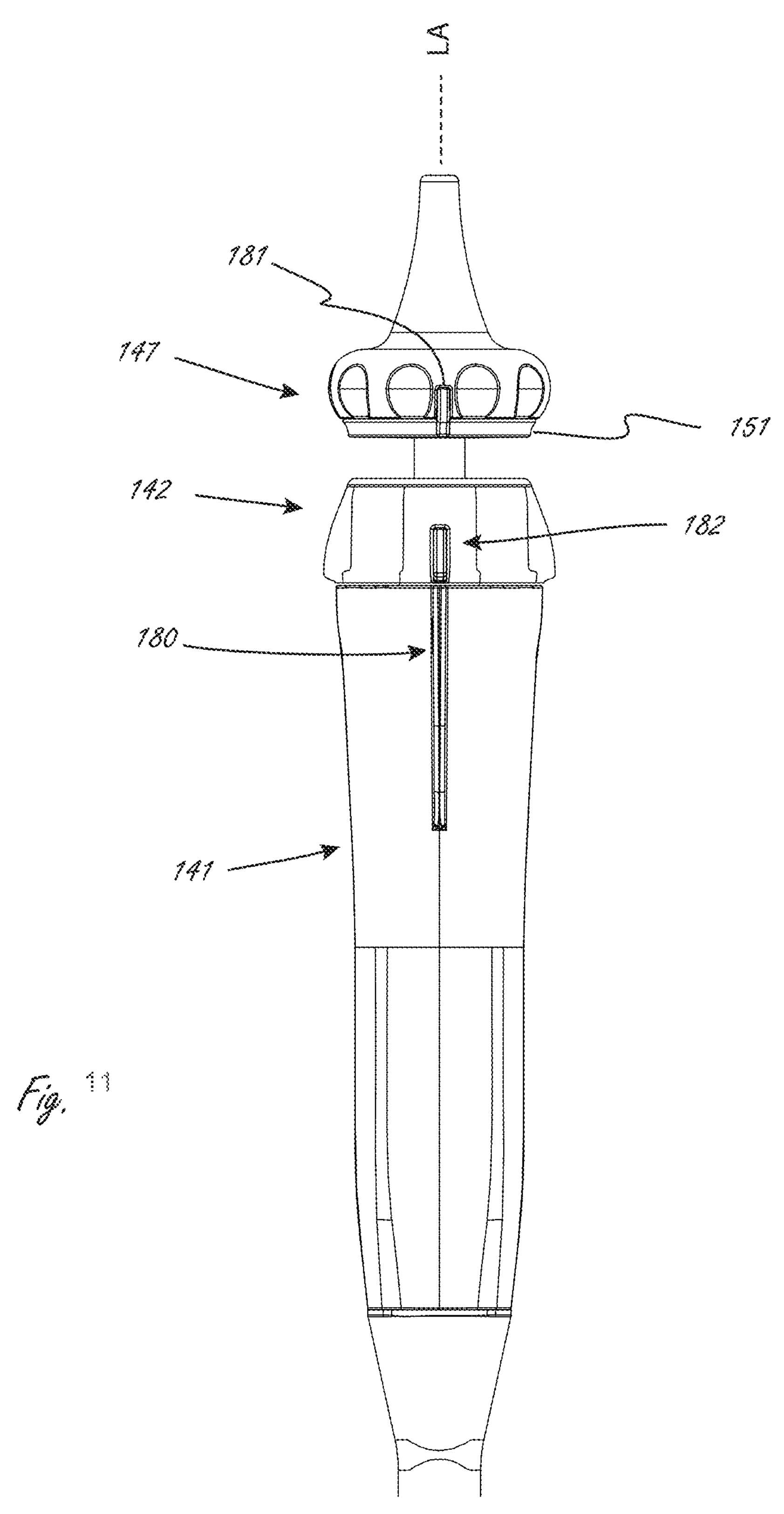
FIG. 11 illustrates an exemplary handle assembly that includes rotation indicators for first and second actuators.

Handle assembly 140 also includes a rotation indicator 180 that can be used to show a user the extent to which at least one of the first actuator and the second actuator are rotated relative to a home, or neutral position. First actuator 143 can include a rotation indicator 181 that is aligned along an axis with rotation indicator 180 when first actuator 143 is in a neutral position, as shown in FIG. 11. When first actuator 143 is rotated, rotation indicator 181 is rotated relative to the axis along which rotation indicator 180 extends, which enables the user to visually understand that first actuator 143, and thus the outer shaft, is rotated to some extend relative to the neutral position. Similarly, second actuator 142 can also have rotation indicator 182 that is aligned along an axis with rotation indicator 180 when second actuator 142 is in a neutral position, as shown in FIG. 11. When second actuator 143 is rotated, rotation indicator 182 is rotated relative to the axis along which rotation indicator 180 extends, which enables the user to visually understand that second actuator 143, and thus the inner shaft, is deflected to some extent relative to its neutral position.

In some alternative embodiments, the handle assembly can include one or more sensors to track how much rotation has occurred for the outer shaft, or how much deflection has occurred in the inner shaft. In some embodiments the handle assembly can include an encoder for each actuator.

In any of the embodiments herein that include an outer shaft and an inner shaft, the device can include one or more lubricants between the inner and outer shafts to make it easier to move the inner and outer shafts relative to one another by reducing friction between the two. If the medical device needs to be cleaned for reuse, additional lubricant can be added between the inner and outer shafts after the cleaning process.

In some embodiments herein the medical device may include a flexible member, such as a flexible conductor bundle (which may be referred to herein as a conductor bundle, flex bundle or other similar derivative thereof), coupled to and extending from a distal region (e.g., probe tip) towards a proximal region of the medical device (see, for example, conductor bundle 2020 shown in exemplary FIGS. 4-6G; or bundle 105 from FIG. 9B). A probe tip may include an ultrasound transducer in electrical communication with a flexible conductor bundle. In some embodiments herein (e.g., FIGS. 9A-11), the probe tip and conductor bundle can be axially displaced (proximally and/or distally) by actuation of a handle actuator (e.g., actuator 143 as shown in FIG. 10A). In some instances, the conductor bundle is disposed within an elongate member (e.g., steerable inner elongate body 132; or elongate member 131) and moves axially relative thereto when the probe tip is advanced distally or retracted proximally. When the distal region (e.g., ultrasound probe) and conductor bundle are retracted proximally (after being advanced distally), the conductor bundle may tend to fold up, bunch up, or otherwise bend, near or adjacent to its distal end due to friction between the bundle and, for example, the elongate member (e.g., steerable inner shaft 132) in which the conductor bundle is disposed. Bunching may occur if the medical device is in a straight configuration as well as if the medical device has some degree of bend (e.g., after being deflected from a straight or linear configuration).

To reduce the degree of, or even prevent completely, a tendency to bunch up or bend, any of the medical devices herein may include a structural tensioning member that is adapted and configured to apply or maintain tension on the flexible member, such as a flexible conductor bundle, at a location that is proximal to where the conductor bundle is coupled to the distal medical tool. By tensioning the flexible member, folding or bunching up of the flexible member can be minimized or even prevented. When used in this context, the "tensioning" member is adapted and configured to reduce distal region(s) of the flexible conductor from bunching (compared to a device without a tensioning member) by proximally moving at least a distal portion of the flexible conductor bundle as the distal probe is retracted proximally. In some embodiments, the structural tensioning member (e.g., a tensioning bar) may be physically secured to the flexible conductor bundle (e.g., direct or indirect attachment). In general, the tensioning members herein are in operable communication with the flexible members (e.g., a flex conductor bundle) such that movement or actuation of the tensioning member applies some force to the flexible member, and may cause movement (e.g., proximal) of the flexible member. In some exemplary embodiments the structural tensioning member may be disposed in or carried by the handle assembly of the medical device. Structural tensioning member in this context may be a single component or an assembly of separate components.

FIGS. 12A-12F illustrate a handle assembly portion of an exemplary medical device, which may be incorporated into any suitable medical device herein. For example, the handle assembly in FIGS. 12A-12F may be part of a medical device that includes a medical tool (e.g., an ultrasound imaging probe) at its distal end or near its distal end, examples of which are described herein. Any other embodiment or feature herein is incorporated by reference into the exemplary handle assembly shown in FIGS. 12A-12F.

Figures 12A, 12D:
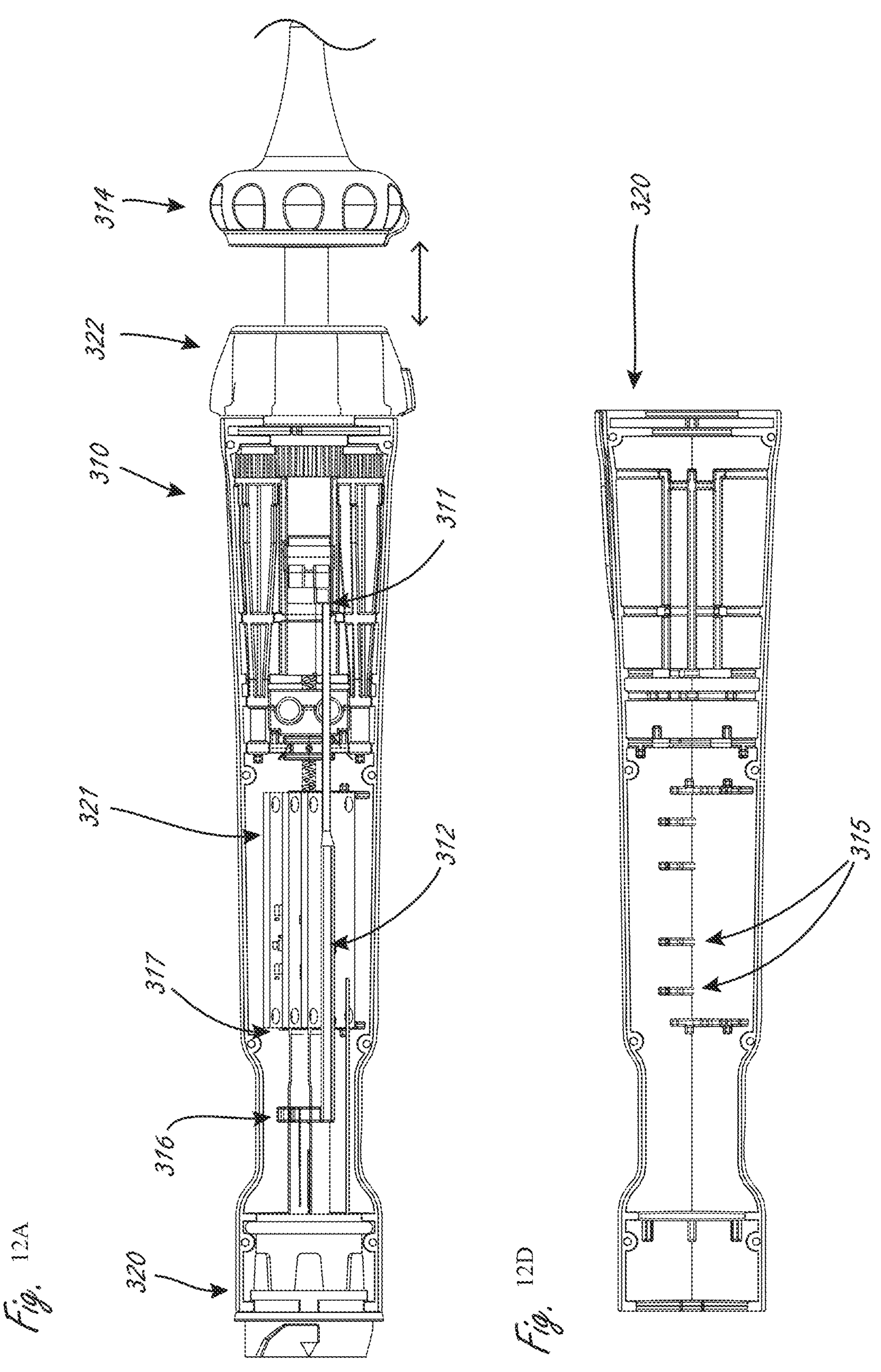
FIG. 12A illustrates internal components of an exemplary handle assembly that includes a tensioning member, or flattening member.
FIG. 12D illustrates internal components of an exemplary handle shell that include one or more guiding features positioned to help stabilize a tensioning member in the handle assembly.

Exemplary handle assembly 310 includes first actuator 314 and second actuator 322, where first actuator 314 is distal to proximal actuator 322. First actuator 314 is adapted and configured to be moved axially (distally and proximally) relative to second actuator 322 (and optionally also rotatable relative thereto), and may be in operable communication with an elongate body (e.g., 131 or 132) that may include a medical tool (e.g., 103) in a distal region. Handle assembly 310 (including actuators) may incorporate any of the relevant disclosure from any other handle assembly herein. The medical device of which handle assembly 310 is a part also includes a flexible member (e.g., flexible conductor bundle 105 in FIG. 9B) securely coupled to (directly or indirectly) the medical tool at a first distal location (e.g., as shown in FIGS. 9B and 9C where medical tool 103 is secured to flexible member 105) and extends proximally from the medical tool towards handle assembly 310. The flexible member may be a flexible conductor bundle and can extend into handle assembly 310, as shown. A portion of the flexible member is disposed within an outer surface of the elongate body (e.g., within 131 and/or 132). The medical device also includes tensioning member that is secured to the flexible member at a second location 316, which is proximal to the first location ("first location" in this context may be referred to as a first distal location or derivative thereof). FIG. 12A illustrates exemplary tensioning member 312, while reference number 312 in FIG. 12A also points to an optional elongate rigid member (in this embodiment the elongate rigid member is linear and extending axially) of the tensioning member. Tensioning member 312 is adapted and configured to tension the flexible member as the medical tool is retracted proximally. This may be referred herein as applying a tensile force to the flexible member, or tensioning the flexible member, or maintaining tension in the flexible member. In this exemplary embodiment, tensioning member 312 is adapted and configured to tension the flexible member as the medical tool is retracted proximally, which in this embodiment occurs when first actuator 314 is retracted proximally from its position shown in FIG. 12A-C. The tensioning members herein can apply tension when the medical device is in a straight configuration and when the medical device is in a non-straight (linear) configuration, such as when the device may be deflected or bent.

In this embodiment, tensioning member 312 (which may include the tensioning bar shown in FIG. 12A) is secured to (e.g., attached directly) the flexible conductor bundle at location 316, the location of which is inside the handle assembly in this embodiment. A tensioning member may alternatively be secured to the flexible member at a location that is not within a handle, such as outside of the handle, such as inside one or both of outer and inner shafts. In this embodiment the tensioning member is also axially secured relative to first actuator 314, such that axial movement of first actuator 314 causes axial movement of tensioning member 312 (which may be in a 1:1 movement ratio). Because tensioning member 312 is also secured to the flexible member (e.g., at location 316), axially movement of tensioning member 312 also causes axial movement of the flexible member at location 316. By securing tensioning member 312 to the flexible member, the flexible member is tensioned distal to where the tensioning member is secured to the flexible member when first actuator 314 is retracted proximally, which prevents the flexible member from folding or bunching up at its distal region near or adjacent to the medical tool (or at least reduces the extent of folding/bunching up compared to a device without a tensioning member).

The flexible member may include a flexible conductor bundle, such as any of the flexible conductor bundles herein. In FIGS. 12A-F, the tensioning member comprises a rigid elongate member (generally referred to as 312 in FIG. 12A) with a fixed length. The rigid tensioning member as shown has a general longitudinal axis, which in this embodiment is parallel with a longitudinal axis of the medical device and/or a longitudinal axis of the handle assembly. The rigid tensioning member may be made of a variety of materials, such as a rigid plastic member.

The tensioning members herein can ensure that the distance traveled by the medical tool is the same as the distance traveled by any point on the flexible member between the first and second locations. The tensioning members herein can ensure that the distance traveled by the medical tool is the same as the distance traveled by the location where the tensioning member is secured to the flexible member (e.g., location 316 in FIG. 12A).

The secured relationship between the tensioning member and the flexible member maintains the flexible member in a substantially flat or straight configuration between the first and second locations as the medical tool is retracted proximally (when the medical device is a straight configuration). A flat configuration in this context can include embodiments in which the flexible member may also be twisted (i.e., the flexible member can be flat and still be twisted, but not bunched/folded). A flattened configuration as used herein indicates a lack of a fold or bunching of the flexible member.

Medical devices in which a tensioning member is incorporated may also be steerable or deflectable. The tensioning members herein can be adapted and configured to apply a tensile force to the flexible member even if the medical device, including the flexible member, are in non-straight (e.g., deflected, steered, bent) configurations. When this disclosure refers to maintaining a substantially flat configuration in the flexible member, it refers to instances where the medical device may be in a straight configuration, which need not be the case, such as when a medical device has been steered, bent, or deflected.

The secured relationship between the tensioning members and the flexible members herein prevents the flexible member from forming a fold (i.e., bending, or bunching up) between the first and second locations as the medical tool is retracted proximally. Folding, bending, and bunching-up in this context includes a first region of the flexible member axially overlapping with a second region of the flexible member, and also includes general bending and bunching of the flexible member, such as regions of the flexible member that are not flat and, for example, form a bend, curved region, and/or meander back and forth.

The flexible member may have flat top and bottom surfaces (e.g., a conductor bundle with one or more flat surfaces), and optionally the tensioning member may be secured to at least one of the top and bottom surfaces. For example, FIGS. 6A-6G illustrate a flexible member with flat or generally flat first and second surface (e.g., top and bottom surfaces), and a tensioning member may be secured to one or both of the flat or generally flat surfaces (e.g., such as at location 316). They may be secured using a variety of techniques, such as using adhesive, welding, or other bonding techniques.

The tensioning member may be in operative communication (directly or indirectly) with a handle actuator such that axial movement of the actuator axially moves the tensioning member. The handle actuator may be further adapted and configured to be rotated (e.g., actuator 314) to cause rotation of the medical tool, and optionally wherein rotation of the actuator does not cause rotation of the tensioning member. The tensioning member can thus be adapted to be moved axially when the actuator is moved axially, but not to rotate when the actuator is rotated. This can be accomplished by the manner in which the tensioning member is operatively in communication (directly or indirectly) with the actuator.

The medical device may include an inner elongate body (e.g., 132) including a lumen in which at least a portion of the flexible member is disposed. An inner elongate body may be independently steerable, such as with a separate independently actuatable handle actuator (e.g., actuator 322). Aspects of other embodiments herein in which the medical device includes an inner member and outer member, the inner member independently controllable (e.g., axially and rotationally) are fully incorporated in any of the embodiments herein.

The flexible member may be coupled to a printed circuit board (e.g., 321 "boards" as shown in FIG. 12A) in the handle assembly. The tensioning member may be coupled to a flexible member proximal to a printed circuit board. In alternative embodiments the tensioning member may be coupled to a flexible member distal to a printed circuit board.

FIGS. 12A-12F is an example of a portion of a medical device that includes an elongate outer body (e.g., 131) including a probe tip in a distal region of the elongate body;

a flexible conductor bundle (e.g., 105) securely coupled to the probe tip at a first location (shown in figure FIGS. 9B and 9C) and extending proximally from the medical tool and into a handle assembly, the flexible member disposed within an outer surface of the elongate body; an inner elongate body (e.g., 131), at least a portion of which is disposed within the elongate outer body, the inner elongate body optionally steerable, wherein at least a portion of the flexible conductor bundle is disposed within the inner elongate body and configured to be axially movable relative to the inner elongate body; a tensioning member secured to the flexible member at a second location in the handle assembly, the tensioning member adapted and configured to apply tension on the flexible member as the probe tip is retracted proximally. Probe tips as used herein may include one or more ultrasound transducers.

Figures 12B, 12C, 12E, 12F:
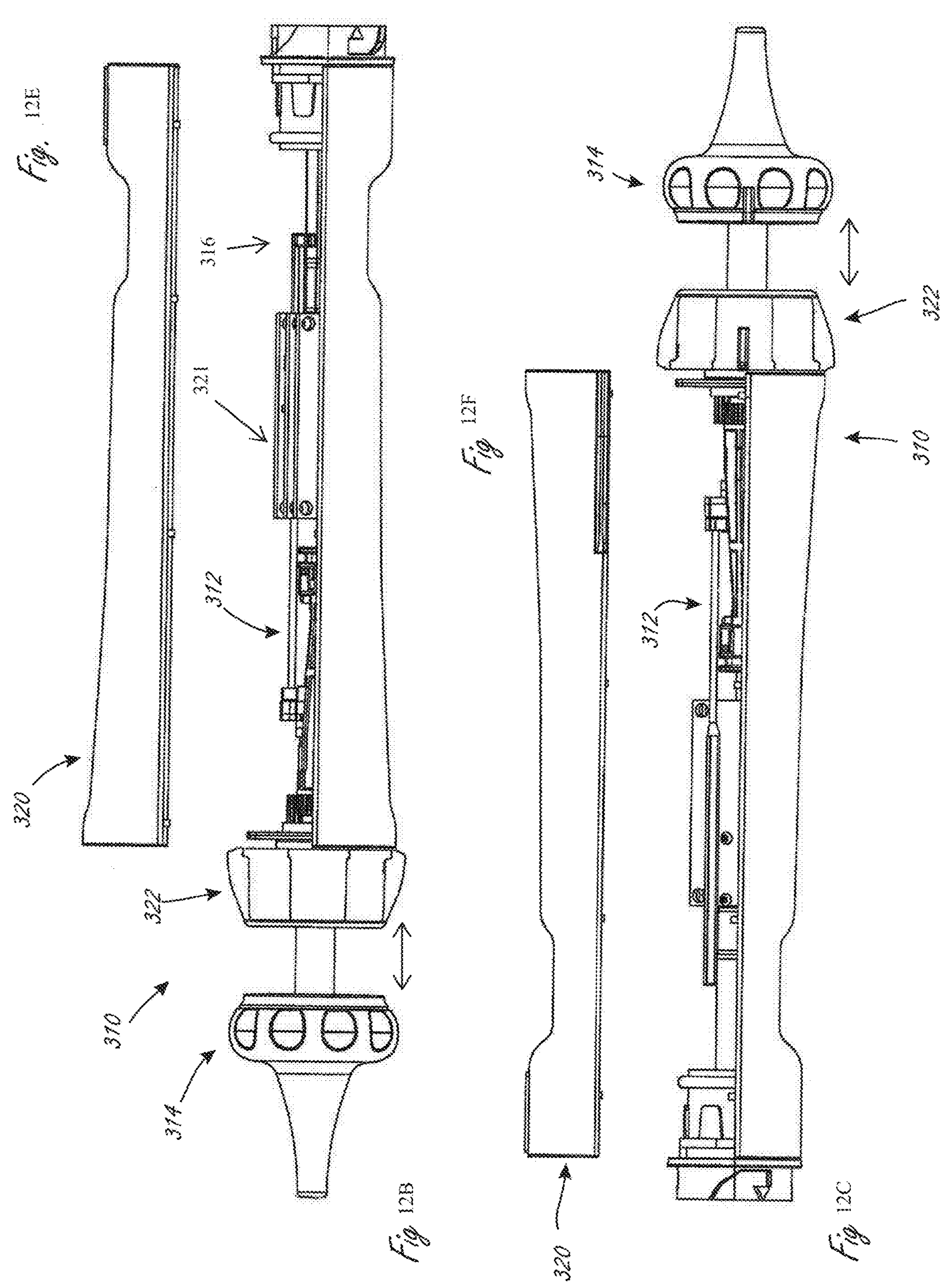
FIG. 12B illustrates (in a side view) internal components of an exemplary handle assembly that includes a tensioning member, or flattening member.
FIG. 12C illustrates (in a side view that is the other side relative to FIG. 12B) internal components of an exemplary handle assembly that includes a tensioning member, or flattening member.
FIG. 12E illustrates a side view of an exemplary handle shell.
FIG. 12F illustrates a side view of an exemplary handle shell.
Figures 13A, 13B, 13C:
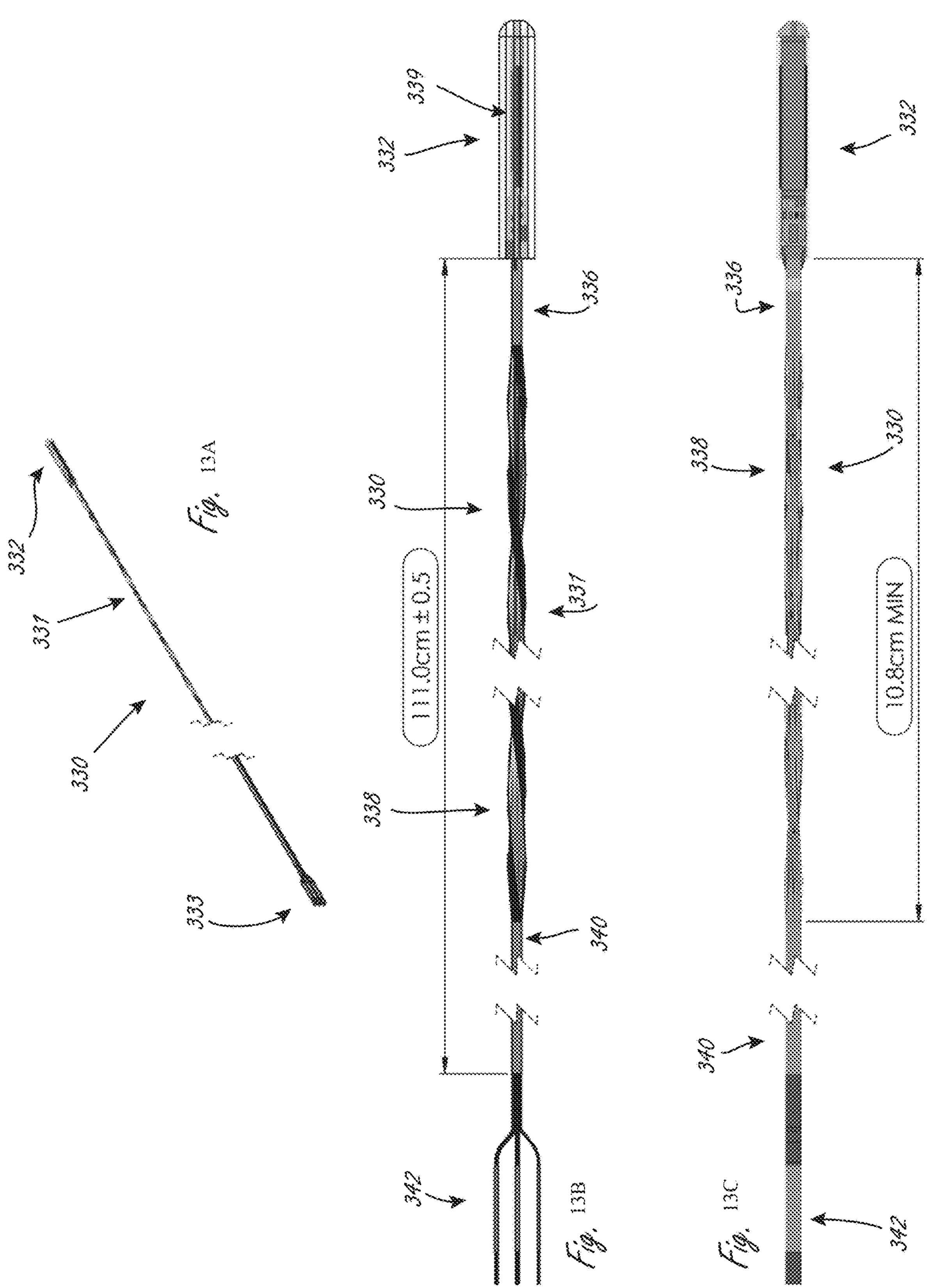
FIG. 13A illustrates an exemplary flexible cable bundle with at least a portion that is twisted relative to a long axis.
FIG. 13B illustrates an exemplary flexible cable bundle with at least a portion that is twisted relative to a long axis.
FIG. 13C illustrates an exemplary flexible cable bundle with at least a portion that is twisted relative to a long axis.
Figures 13D, 13E:
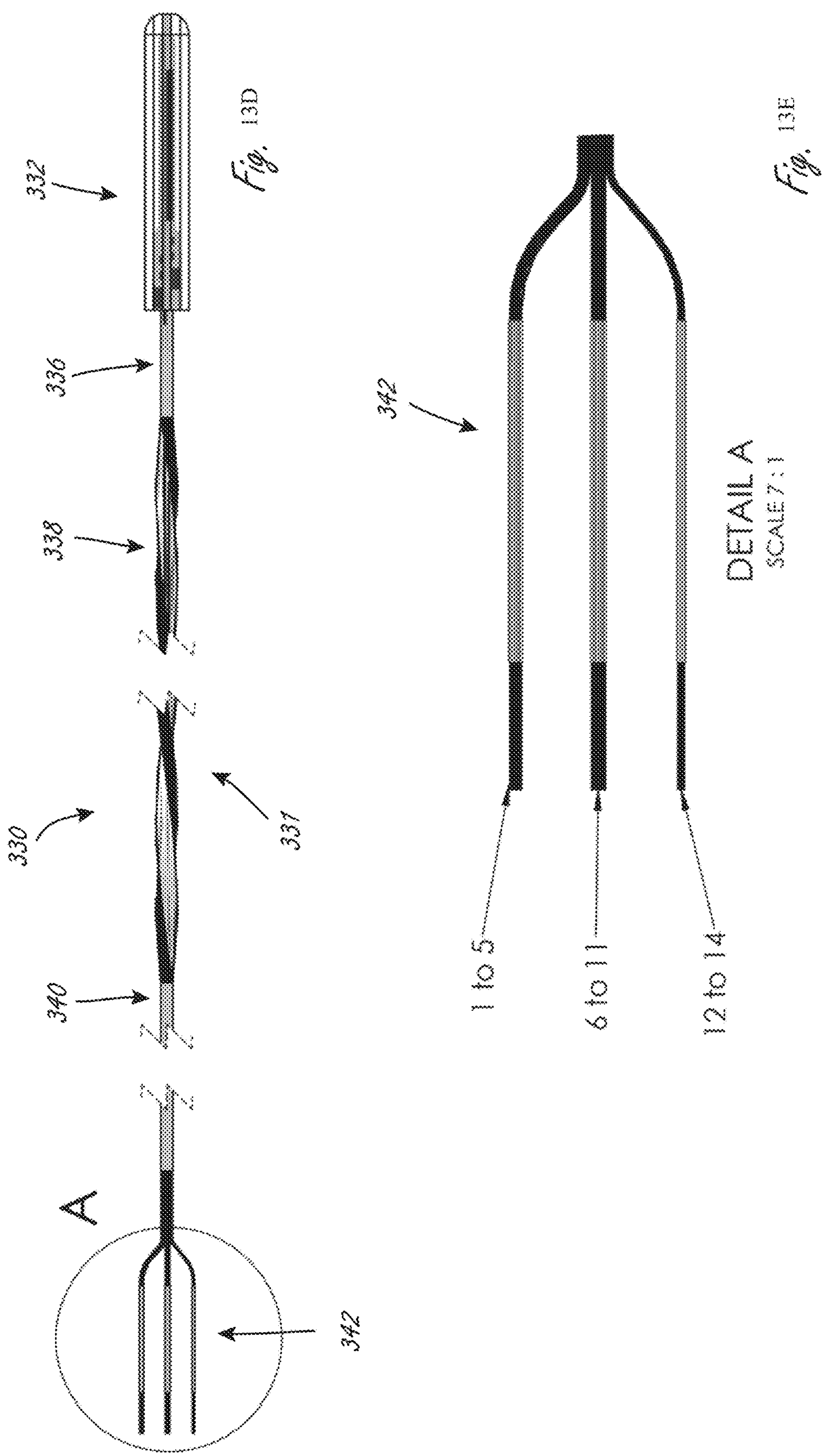
FIG. 13D illustrates an exemplary flexible cable bundle with at least a portion that is twisted relative to a long axis.
FIG. 13E illustrates a detail from FIG. 13D.

FIGS. 12E-F illustrate a half of a handle outer shell 320, two of which form a portion of the outer surfaces of the handle assembly 310. Handle shells 320 include radially inwardly extending features 315 that are adapted to interface with a control the movement of the tensioning member 312. Features 315 can include guides that are configured to interface with the tensioning member at one or more locations and help stabilize the tensioning member.

Any other handle assembly component in any other embodiment herein that can be suitably integrated into handle assembly 310 is incorporated by reference herein.

In any of the embodiments and claims herein, the phrase "tensioning member" may be replaced with "straightening member," "flattening member," or a derivative thereof. As described herein, a straightening member or flattening member refers to maintaining a substantially straight or flattened configuration in the flexible member when the medical device is in a straightened configuration, and does not require that the device always has a straightened configuration. Thus, even if the flexible member is not necessarily being placed under tension, it may still be maintained in a straightened (i.e., not folded configuration) along at least a portion of its length due to a straightening member. Member 312 in FIG. 12A, for example, is an example of a straightening member, even if it also functions as a tensioning member. This applies to all tensioning members described, shown, and claimed herein. In some embodiments herein, the "member" can be a straightening member (or flattening member) and can also function as a tensioning member. Additionally, the phrase "tensioning member" herein may be replaced with "fold-prevention member," "bend-prevention member," "bunching-prevention member," or a derivative thereof.

The disclosure above describes that in some embodiments the flexible member, such as conductor bundle 2010, may be twisted along a portion of its length. For example, a conductor bundle may be twisted to provide a more balanced cross-section along a portion of the length of the medical device. A conductor bundle may be twisted only in a portion of the medical device that will experience deflection.

FIGS. 13A-13E illustrate a portion of an exemplary medical device that includes a twisted flexible member, such as a flexible conductor bundle. The embodiment in FIGS. 13A-E may be incorporated with any other suitable feature and/or medical device described herein.

The portion 330 of the medical device shown in FIGS. 13A-E includes a medical tool 332 at a distal region, a flexible member 331 coupled thereto and extending proximally therefrom, and a proximal end region 333 comprising a plurality of electrical connectors. Flexible member 331 may be a flexible conductor bundle, such as any of the bundles herein. Medical tool 332 may include an ultrasound imaging transducer 339. Flexible conductor bundle 331 has a region 338 in which the conductor bundle is twisted, the twisted region 338 having a distal end and a proximal end. Flexible conductor bundle 331 also includes a region 336 distal to twisted region 334 that is not twisted, and a region 340 proximal to twisted region 336 that is not twisted. Medical tool 332 may be coupled to an outer shaft, such as outer shaft 131 shown in FIG. 9B.

The length of twisted region 338 from its distal end to its proximal end can vary, and in some embodiments is from 5-15 cm, such as from 8-15 cm, such as 11 cm. The length over which a complete turn is formed can vary well, such as from 1-5 cm, such as 3 cm.

The number of twists over the length of the twisted region can vary as well, such as, for example without limitation, 7-9 full twists.

An exemplary manner in which to form the twisted region of the flexible member (e.g., flexible conductor bundle) is to couple the flexible member to the medical tool at the distal end (e.g., probe tip). A thin section of PET heat shrink may then be advanced over the flexible conductor bundle. A portion of the device can be held in place while another portion is twisted to the desired number of turns to form the twisted region. While the twisted configuration is maintained, the PET can be heat shrunk over the twisted bundle region. Additional layers of PET may be subsequently added. An elongate member (e.g., shaft 131) may then be placed over the bundle, including the twisted region, and the elongate member can be bonded to the medical tool.

The concepts that follow may be applied to any suitable device, system, and/or method of use set forth above. While the disclosure that follows is described generally in the context of imaging catheters, and in particular ultrasound imaging catheters, the concepts that follow may be applied to any type of suitable medical device that includes a cable through which electrical signals are transmitted. One merely exemplary illustrative medical device is an ultrasound imaging catheter, which includes a cable bundle in electrical communication with one more ultrasound transducers, wherein the cable bundle transmits signals to and/or from the ultrasound transducers. Exemplary ultrasound imaging devices, including handles thereof, are shown and described with respect to FIGS. 1-13E herein, the disclosures of which are fully incorporated by reference into the disclosure that follows. For example, the handle assemblies shown in FIGS. 14-20 and descriptions thereof may incorporate any of the disclosure herein related to the handle assemblies in any of FIGS. 1-13E herein.

Figure 14B:
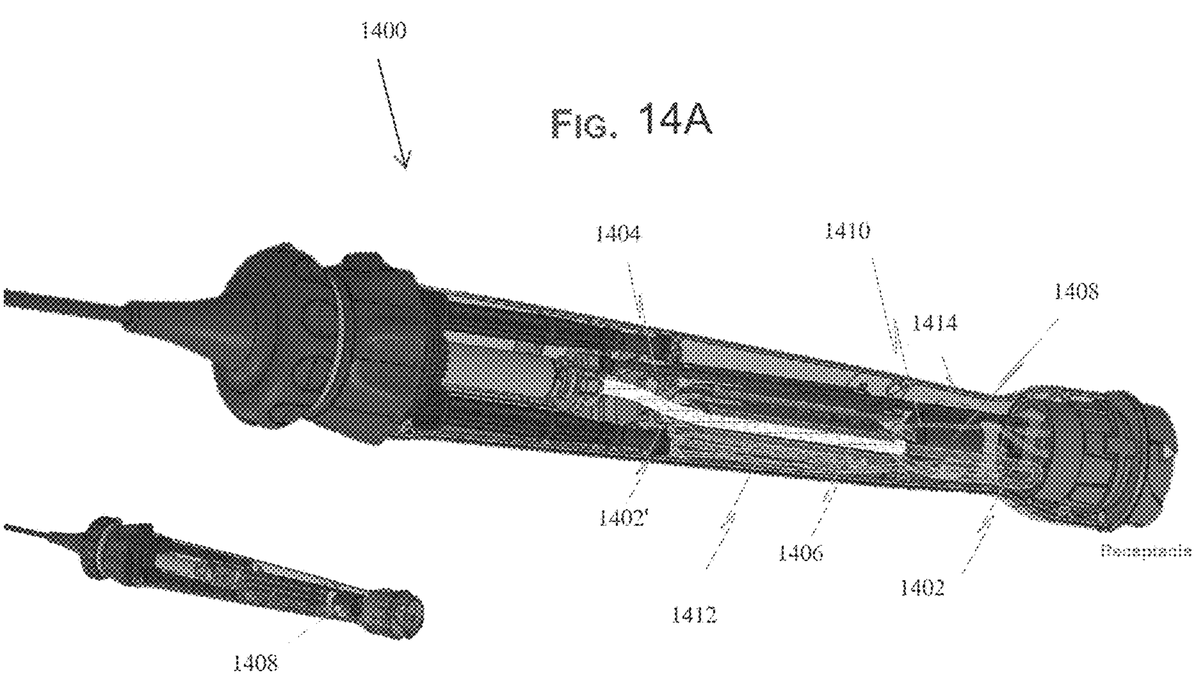

FIGS. 14A and 14B illustrate an exemplary handle 1400 of a medical device, with half of a handle shell removed to show internal handle components. Any of the components in any of the handle assemblies herein may have exemplary designs described in more detail with respect to embodiments in FIGS. 1-13E. For example, flex bundle 1402 in FIGS. 14A and 14B may include any of the disclosure of any of the electrical flexible bundles herein. Additionally, for example, the push arm 1404 in FIG. 1 may include any of the disclosure with respect to any tensioning members herein adapted for maintaining tensioning in the cable bundle. Additionally still, the inner shaft 1406 in FIGS. 14A and 14B may be any of the inner members (or any derivative thereof) herein. Additionally, the device medical extending distally from handle 1400 in FIGS. 14A-20 may also include an outer member or outer shaft, such as any of those described herein. It is further understood that "inner" shaft is illustrative and the medical device shaft does not necessary require an inner shaft and an outer shaft. In embodiments that include an inner shaft and an outer shaft, the two shafts may be axially movable relative to one other to allow for a telescoping probe tip, while in any embodiments herein an inner shaft and an outer shaft may be immovable relative to each other, such as in the example shown in FIG. 20.

Figure 18:
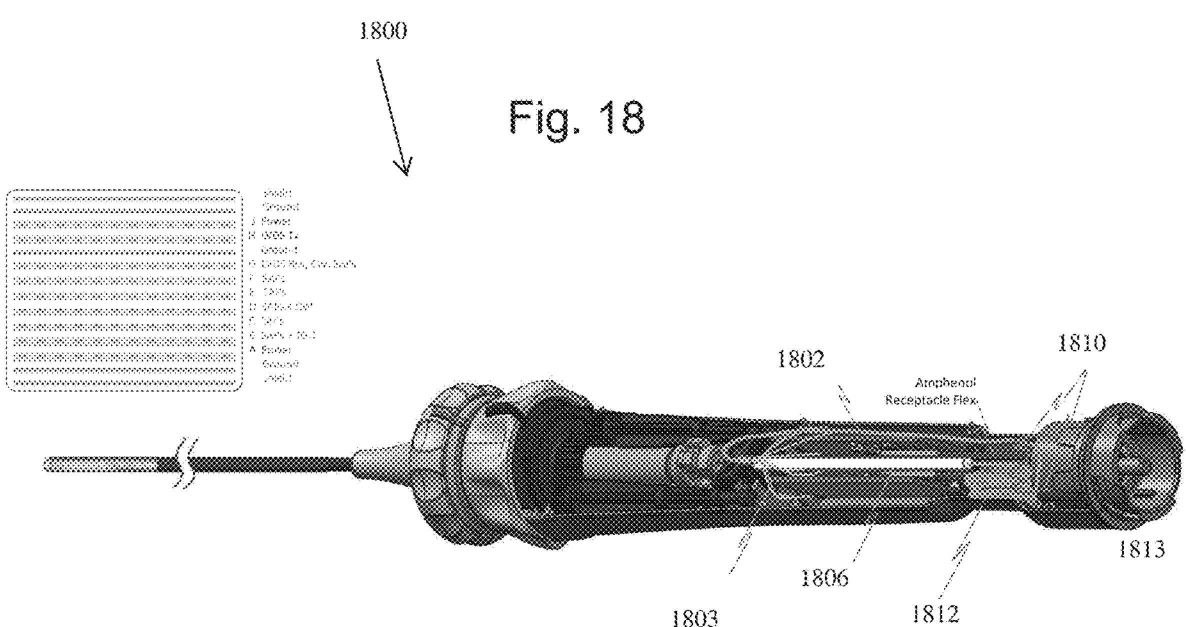
FIG. 18 illustrates an exemplary handle that includes a cable bundle shield layer removed before the bundle passes through a ferrite bead.

Some medical device cables may be susceptible to noise along the cable line(s) in the frequencies of interest. One aspect of the disclosure is related to immunity performance to reduce noise. FIG. 14A illustrates an exemplary handle that includes therein an exemplary electrical noise suppression member 1408 that includes a lumen through which a flexible cable bundle 1402 passes. By way of example only, any of the electrical noise suppression members herein may comprise a ferrite bead, general examples of which are known. This disclosure may refer to a ferrite bead in the context of certain embodiments, but it is understood to be illustrative only and other materials and/or configurations of an electrical noise suppression member may be used. A noise suppression member herein may include one or both of a material or configuration such that it is adapted to increase impedance to any RF noise coupled into sensitive analog lines. It is of note that a cable bundle shield 1410, an example of which is shown in FIG. 18, has been removed from the cable bundle 1402 within the handle before the cable bundle 1402 passes through the electrical noise suppression member 1408 so as not to cause a reduction in the shield 1410 impedance.

While ferrite beads are described in examples herein, these are understood to be examples and other materials and/or configurations may be used. In general, the noise suppression members herein include a material that is configured to surround one or more signal line conductors such that the surrounding material provides a high impedance pathway intended to dissipate frequencies in a targeted range that are induced in the surrounding material from the signal line. The dissipation of the frequencies provides a filtering or noise-suppression effect. The surrounding material may comprise sintered powders and may be formed into a hollow cylindrical or similar extruded polygonal shape. The material may be formed as one piece with the signal line conductor running through the middle, and in some embodiments include two halves clamped together over the signal line conductor. The impedance and filtering effects of the surrounding material may be optimized based on the selection, size, and relative amounts of the sintered powders. The powders are typically formed into a ceramic compound comprising a mix of iron oxide and other materials such as cobalt, copper, manganese, magnesium, nickel, and zinc. The circumference, thickness, and length of the surrounding material may also be optimized for the desired effect. The signal line (e.g., cable bundles herein) may pass once through the middle or, after passing through once, may be routed around the outside of the surrounding material and back through the center in the same direction as the first pass (forming a winding) multiple times. The various constructions and configurations allow optimization of the impedance at a given frequency range. In some applications of intracardiac ultrasound imaging, ferrite construction may be selected to provide enhanced immunity from frequencies<10 MHz and to suppress radiation of frequencies>100 MHz. Different surrounding material embodiments may be employed at different locations along the pathway of the signal line conductor (cable bundles herein) to achieve different noise suppression effects.

One aspect of this disclosure is related to improving emissions within a handle of a medical device. FIGS. 14A and 18 illustrate examples in which excess flex cable bundle 1402 is disposed in the handle and is folded in folded region 1412 in an organized manner in the handle, and in this embodiment is folded in an accordion style configuration as shown against an inner surface of a shell of handle 1400. As shown, cable bundle shield 1410 is routed out of the cable bundle 1402 before the bundle assumes its folded configuration in region 1412, as shown. Separating the shield layer 1410 from the rest of the bundle 1402 before folding in region 1412 minimizes inductance of shield layer 1410 while increasing impedance of signal cables in the frequencies of interest. Folding the excess cable length in an accordion style fold as shown can reduce unit to unit variation, minimizes self-inductance of the signal cable and can help reduce radiated emissions. In some embodiments herein, however, the cable bundle may not be folded within the handle, an example of which is shown in the exemplary embodiment in FIG. 20.

A ferrite bead 1408 in FIG. 14A that is disposed within the handle 1400 is positioned about or around the portion of the flex cable bundle 1402 that contains the signal lines and grounds, but not the shield 1410, as shown. An exemplary advantage to this construction may be to increase impedance to RF entering the cable bundle (for noise reduction) without increasing impedance to the shield 1410. The shield impedance should be as low as possible to shunt out any RF current picked up. By removing the shield 1410 from the cable bundle 1402 in the handle before it passes through the ferrite bead 1408, the ferrite bead 1408 does not increase the impedance of the cable bundle shield 1410. Section of the cable bundle 1402' are shown fanned out to attachment locations on the printed circuit boards ("PCBs") with the handle. A receptacle flex 1414 is also shown coupled to the receptacle at the handle proximal end. FIG. 14B illustrate the handle and labels noise suppression member 1410 without showing the cable bundle for clarity.

The ferrite (or other suitable noise suppression member/material) can improve immunity to outside noise, such as in the 5-10 MHz imaging frequency if the system is so configured. A ferrite bead can be selected to maximize impedance in a desired frequency range (e.g., 5-10 MHz), while allowing it to fit in the handle shell. An exemplary impedance obtained is ~90-102 ohms in the range of interest. The impedance can be increased by increasing the number of "turns", or "T", defined as how many times the cable passes through the inside of the ferrite. The impedance increases with the square of the number of turns. The cable may pass 1 T through the ferrite, although it could be turned 2, 3, or 4, up to the limit of the ferrite ID. An alternative to the solid ferrite is to have a "split" ferrite which is clamped around the cable. This could allow ACF bonding and then wrapping of the cable. 1 T within a solid ferrite may be adequate to adequately improve noise immunity. Additionally, for a solid core, if the cable is wrapped around the ferrite, there may not have enough slack for an ACF bonding process. In an exemplary implementation, too much impedance in the desired frequency may have a negative effect on, for example, image quality.

As shown in FIG. 14A, excess cable bundle may be folded in a controlled and organized manner or configuration within the handle. For example, an "accordion" style fold as shown in FIG. 14A may minimize looping and any RF being inducted back into the flex bundle. Ribs or other protruding members may be added directly into (e.g. formed integrally with) the inner surface of the handle shell to facilitate folding of the flex cable bundle. An alternative embodiment is a separate non-integral handle component to facilitate the flex cable folding.

Figure 15:
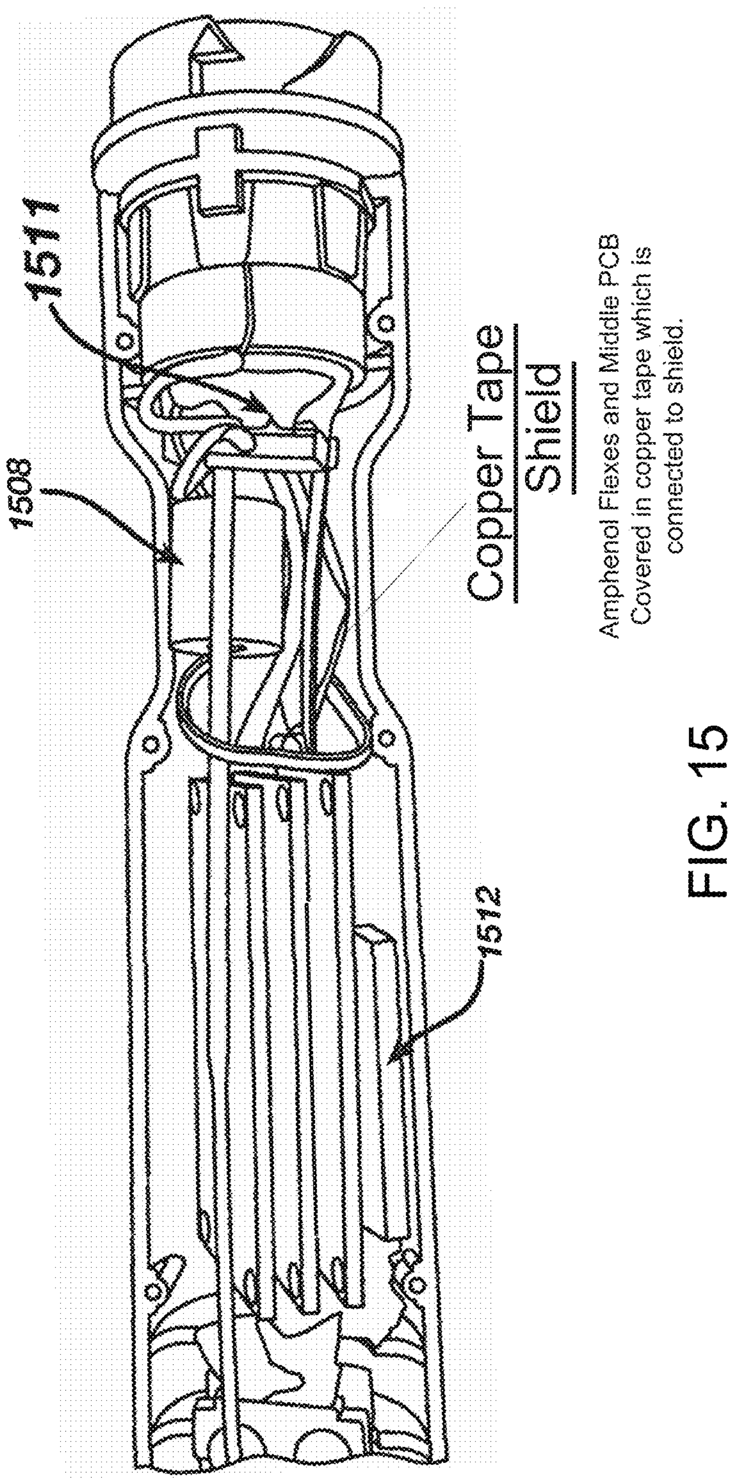
FIG. 15 illustrates an exemplary handle that includes a cable bundle shield layer removed before the bundle passes through a ferrite bead.
Figure 17:
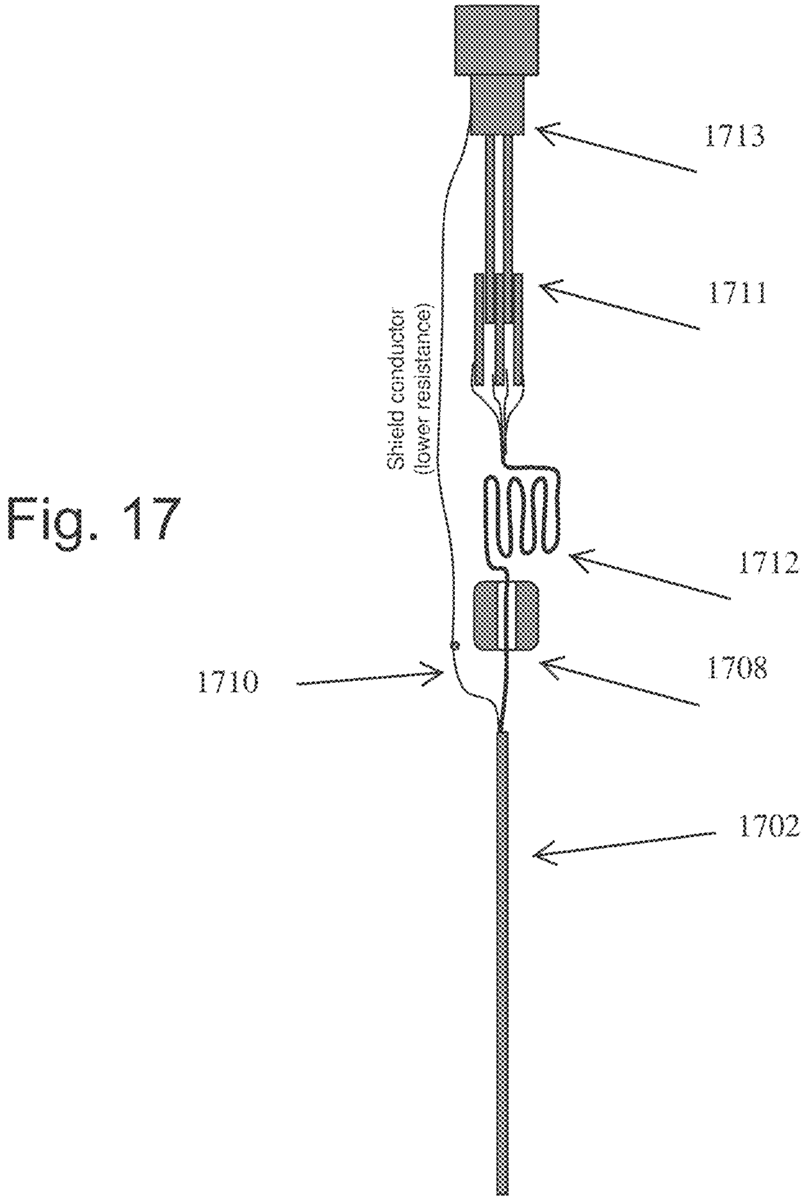
FIG. 17 illustrates an exemplary schematic of cable routing.

As noted above, the shield is pulled out of or removed from the cable bundle, as shown in exemplary FIG. 14A and FIG. 17. Both the top and bottom shield strip are shorted to a single wire, which is soldered to the plated surface of the receptacle, as shown in FIGS. 14A and 15 (at location 1511). This plating makes the shield connection to the umbilical cable plug. Exemplary benefits of this approach can include one or more of the following: transmitting RF out of the device in as low an impedance path as possible; preventing the shield from entering the ferrite; or minimize looping of the shield near the other conductors which would provide more noise inductance into the conductors.

FIGS. 14A and 15 illustrate an exemplary embodiment of an imaging catheter with optional tensioning controlling push arm, which may include any of the disclosure of the tensioning members set forth herein (e.g., with respect to any of FIGS. 1-13). A push arm may be present in catheter designs in which an inner shaft and an outer shaft are movable relative to each other. In these embodiments, the cable bundle may be left intact (shields and remainder of flexes) between the exit out of the inner shaft and the push arm attachment to allow the bundle to telescope back and forth with the distal tip (2.5-3.0 cm), which may have an ultrasound transducer therein. Tension to the bundle is provided from the tip during advancement, while tension during retraction is provided from the point of push arm attachment. An additional intact portion (another 2-3 cm) proximal to the push arm attachment can be provided to allow changing of the bundle radius during advancement and retraction. While the shield could be pulled out of the bundle at the push arm attachment, it may be preferred to pull it out after the additional 2-3 cm to prevent it from having to move. The shield exit can be secured, and the remaining cable immediately routed into the noise suppression member.

A distal tip of the medical device, such as any of the distal tips herein that include an ultrasound probe, may include shielding. For example, some medical device tips can include an ultrasound transducer. Shield strips may be extended around the tip (along the existing short flex strips), except for where the acoustic window is. The shield may also be wrapped around the sides of the transducer. Tip flex strips may also be plated or coated in a conductive material connected to the shield conductors. A very thin shield coating could be provided over the transducer at least ¼-⅛ the ultrasound wavelength.

Some embodiments may include additional shield layers incorporated into the layers of the PCBs and flex circuit extending between the PCBs and catheter connector. The shielding may also be applied externally to the PCBs and flex circuit using copper tape or other similar construction. The additional shielding layers can be connected to the catheter connector shield directly, or via the low impedance shield connection wire (FIG. 18). In another embodiment, the low impedance shield connection wire may terminate in the distal side of the additional shielding layers and the proximal end of the additional shielding layers terminated to the connector shield layer. Terminations may be made through the use of solder, welding, a mechanical contact, or other conventional techniques, for example.

Some embodiments may include an umbilical connector shielding. A connection may be made between the catheter and cable shield through a plated surface of the catheter receptacle and umbilical plug. A lower impedance connection may be preferred to be added to or provided instead of the existing plated connection. For example, the central core of the receptacle and plug could be adapted to provide a direct electrical connection to one another. A "banana style" connection could be made or other pogo-pin, c-pin, or lever arm metal-metal mechanical connection made. In lieu or in addition to shield plating, directed braided wire (flat shield wire preferred) could be electrically attached (solder, crimp, or the like) between the connector pins and the shields in the umbilical cable and catheter. The umbilical cable plug could have a recessed, touch proof receptacle for a male-style pin from the catheter receptacle connector. This could be positioned on the central axis, but could also be on the inner circumference or integrated into the cable.

Some embodiments may include an umbilical ferrite. A clamp on ferrite may be used over the outside of the umbilical cable to improve noise immunity. A 3 T or 4 T may be used on the cable. This use is common in the art. However, an appropriately sized ferrite may be used under the shield and have it integrated in the design. This may be located at the DLP (console connector) side, outside the DLP, or actually inside the housing (and inside the shielded cage), of the DLP. It may also be incorporated near the plug (catheter connector) side, although the extra weight in this location may not be as desirable and should be considered.

Figure 16:
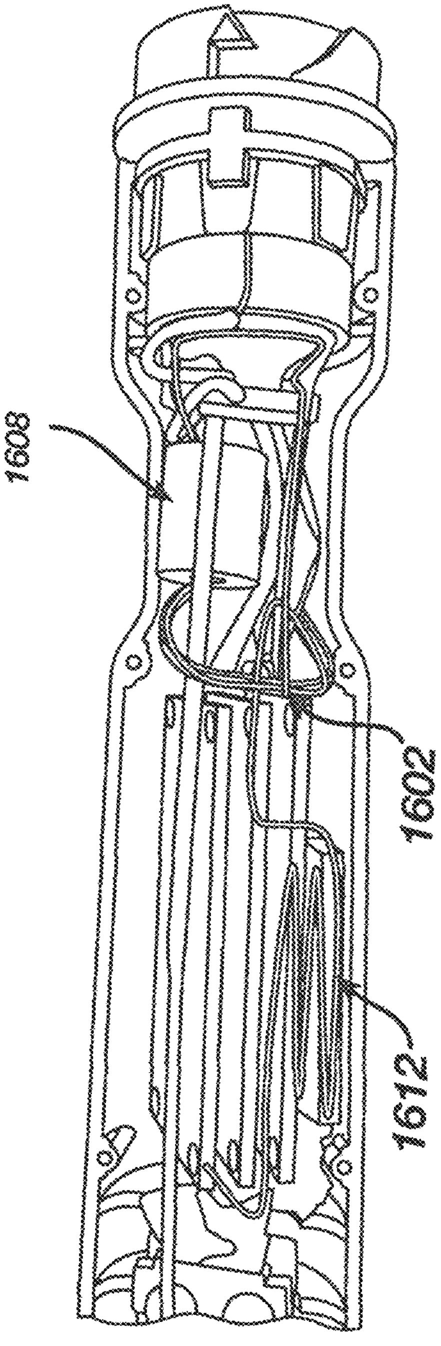
FIG. 16 illustrates an exemplary handle that includes a cable bundle shield layer removed before the bundle passes through a ferrite bead.

FIGS. 15 and 16 illustrate photographs of a portion an exemplary handle shown in FIG. 14A, whereas FIG. 16 additionally highlights an exemplary cable bundle 1602 pathway within the handle, with components similarly labeled with respect to FIGS. 14A, 15, 17, 18 and 19.

FIG. 17 schematically illustrates an exemplary cable bundle 1702 routing within a handle (handle housing not shown) that is shown in FIGS. 14A-16. FIG. 17 excludes the handle housing to provide a more clarified routing pathway. Shield 1710 is removed from cable bundle 1702 before it passes through noise suppression member 1708 (e.g., ferrite bead) and the cable bundle is shown folded in folding region 1712. Sections of the cable bundle are fanned out to attachment locations on the printed circuit boards 711 as shown. Receptacle 1713 is also shown.

FIG. 18 illustrates an exemplary embodiment of an imaging catheter in which handle 1800 does not include a noise suppression member (e.g., ferrite bead) therein. Handle 1800 may include any other handle component or functionality described in any of the other handles herein. For example, exemplary inner shaft 1806 is shown. In this example, shield layers 1810 are routed directly from the cable bundle to the receptacle 1813, as shown. The cable bundle is folded accordion style in folded region 1812. After the shield layers are removed from the bundle, cable bundle 1802 is routed directly to the PCBs as shown, and are fanned out at locations 1803 to the PCB attachment points.

Additional exemplary details and parts are shown, which may be the same or similar to the handle components shown the embodiments in FIGS. 14A-17. Any suitable disclosure from the embodiments from FIGS. 14A-17 may be incorporated by reference into the disclosure of the embodiment shown in FIG. 18. FIG. 18 also illustrates an exemplary cable bundle cross section, wherein any of the embodiments herein may include such as cable bundle. The cable bundle is exemplary, however, and not every layer need be included, in this embodiment or any other embodiment.

Figure 19:
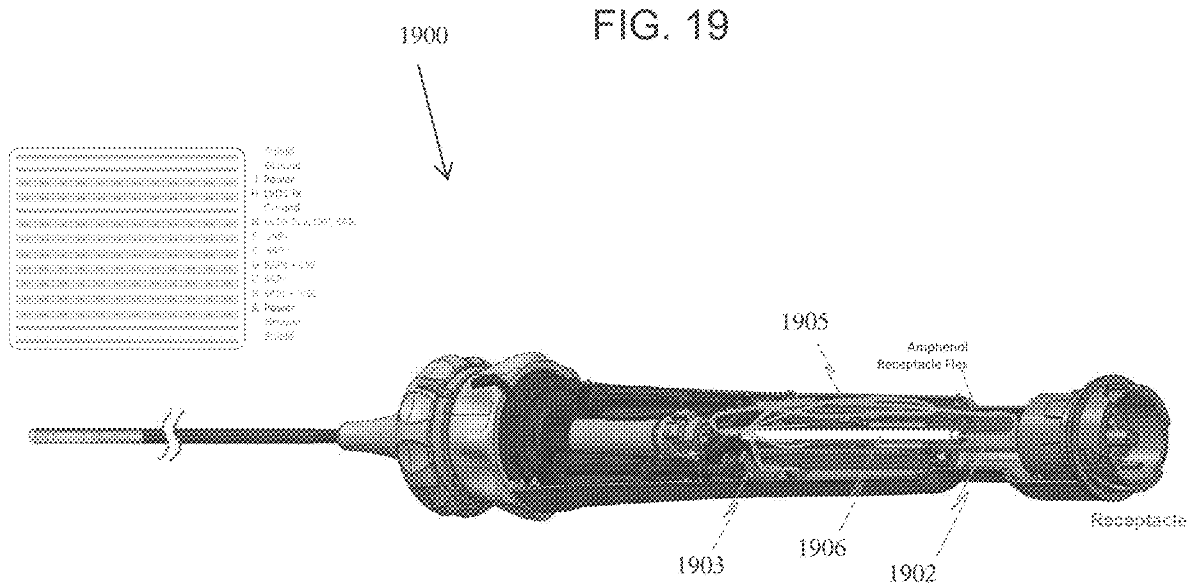
FIG. 19 illustrates flexible cable folding within a handle of the medical device.

FIG. 19 illustrates an exemplary embodiment of an imaging catheter in which handle 1900 does not include a ferrite bead, and wherein excess cable bundle 1902 is looped in looped region 1905. The handle shown in FIG. 19 may incorporate any suitable feature of any of the other handles and imaging catheters herein. Handle 1900 has inner shaft 1906 extending therein, from which cable bundle 1902 extends as shown. The cable bundle is fanned out at locations 1903 for attachment to the PCBs as shown. Handle 1900 may include any other suitable component or functionality described or shown with respect to other handles herein.

Figure 20:
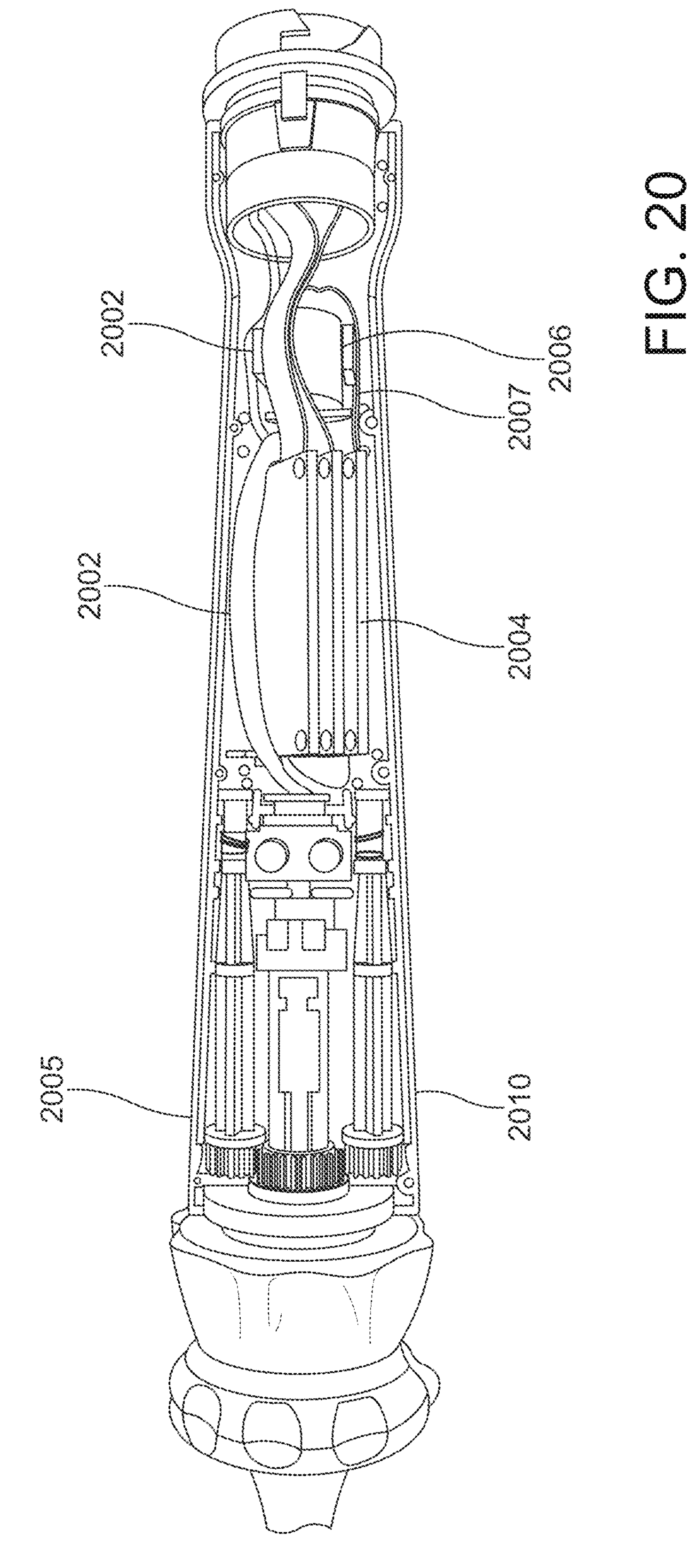
FIG. 20 illustrates an exemplary handle that includes a cable bundle shield layer removed before the bundle passes through a ferrite bead.

FIG. 20 illustrates an exemplary handle 2000, with half of handle housing 2005 removed to illustrate internal components therein. Handle includes catheter shaft control system 2010, which may include any suitable features herein to cause the deflection of a deflectable shaft herein, such as one or more pull wires routed through an elongate deflectable shaft. In this example, flexible cable bundle 2002 extends around a plurality of printed circuit boards 2004. This in contrast to FIG. 14A-19 herein, in which the flexible cable bundle passed between first and second of a plurality of printed circuit boards. In this example, shield 2002 is removed from the cable bundle within the handle before the remainder of the cable bundle passes through ferrite bead 2006, as shown. The bundle 2007 with the shield removed then extends proximally and is coupled to the printed circuit boards 2004, as shown. In the example of FIG. 20, an inner and outer catheter shafts are not axially movable relative to each other (not telescoping) and the cable bundle is not axially movable within the handle after the handle is assembled. The flexible bundle may pass around the printed circuit boards 2004 as shown as the flexible cable bundle does not need to follow a straight axial path for easy axially movement, as may be beneficial in some examples that includes a telescoping probe tip. Routing the flexible cable bundle around the printed circuit boards 2004 may help increase the distance between the signal lines in the cable bundle 2002 and the signal lines (particularly the analog signal lines) in the printed circuit boards 2004 so as to minimize noise pickup.

The invention claimed is:

1. An ultrasound imaging catheter, comprising:

an elongate shaft sized and configured to be advanced within a patient;

a handle adjacent the elongate shaft sized and positioned to remain outside of the patient, the handle including an outer surface configured to be gripped by a user;

a distal tip including an ultrasound transducer;

an elongate cable bundle in communication with the ultrasound transducer, the elongate cable bundle passing through the elongate shaft and extending into the handle, wherein the elongate cable bundle passes through a ferrite bead that is secured within the handle, wherein the ferrite bead is configured to provide between 90 ohms and 102 ohms of impedance at a frequency in the range 5 megahertz (MHz) to 10 MHz, wherein the relationship between the impedance (X), frequency (f), and capacitance (C) is based on $$X = \frac{1}{2\pi fC},$$

and wherein a shield layer of the cable bundle is removed from the elongate cable bundle within the handle at a location such that the shield layer does not pass through the ferrite bead that is secured within the handle.

2. The ultrasound imaging catheter of claim 1, wherein the elongate cable bundle is folded upon itself in a folded region within the handle, and wherein the shield layer has been removed from the cable bundle before the folded region such that the shield layer is not folded within the handle.

3. The ultrasound imaging catheter of claim 1, wherein the shield layer is coupled to a receptacle of the handle.

4. The ultrasound imaging catheter of claim 1, wherein the cable bundle is coupled to a plurality of printed circuit boards that are secured within the handle.

5. The ultrasound imaging catheter of claim 1, wherein the cable bundle extends from a proximal end of an elongate shaft that is disposed within the handle.

6. The ultrasound imaging catheter of claim 1, wherein the cable bundle extends radially outside of a plurality of printed circuit boards that are disposed within the handle.

7. The ultrasound imaging catheter of claim 1, wherein the cable bundle passes between first and second of a plurality of printed circuit boards that are disposed within the handle.

8. The ultrasound imaging catheter of claim 1, wherein the cable bundle includes a movable portion that is axially moveable within the handle.

9. The ultrasound imaging catheter of claim 1, wherein the cable bundle is not adapted to be moved axially within the handle after the handle is assembled.

10. An ultrasound imaging catheter, comprising:

an elongate shaft sized and configured to be advanced within a patient;

a handle adjacent the elongate shaft sized and positioned to remain outside of the patient, the handle including an outer surface configured to be gripped by a user;

a distal tip including an ultrasound transducer;

an elongate cable bundle in communication with the ultrasound transducer, the elongate cable bundle passing proximally through the elongate shaft and extending into the handle comprising an electrical noise suppression member is configured to provide between 90 ohms and 102 ohms of impedance at a frequency in the range 5 megahertz (MHz) to 10 MHz, wherein the relationship between the impedance (X), frequency (f), and capacitance (C) is based on X=wherein the elongate cable bundle is folded upon itself in a folded region within the handle, and wherein a shield layer of the cable is removed from the cable bundle within the handle before the folded region such that the shield layer is not disposed in the folded region.

11. The ultrasound imaging catheter of claim 10, wherein the shield layer is coupled to a receptacle of the handle.

12. The ultrasound imaging catheter of claim 10, wherein the cable bundle is coupled to a plurality of printed circuit boards that are disposed within the handle.

13. The ultrasound imaging catheter of claim 10, wherein the cable bundle extends from a proximal end of an elongate shaft within the handle.

14. The ultrasound imaging catheter of claim 13, wherein the cable bundle extends radially outside of a plurality of printed circuit boards that are disposed within the handle.

15. The ultrasound imaging catheter of claim 13, wherein the cable bundle passes between first and second of a plurality of printed circuit boards that are disposed within the handle.

16. The ultrasound imaging catheter of claim 10, wherein the cable bundle is axially moveable within the handle.

17. The ultrasound imaging catheter of claim 10, wherein the cable bundle is axially immoveable within the handle.

18. An ultrasound imaging catheter, comprising:

an elongate shaft sized and configured to be advanced within a patient;

a handle adjacent the elongate shaft sized and positioned to remain outside of the patient, the handle including an outer surface configured to be gripped by a user;

a distal tip including an ultrasound transducer;

an elongate cable bundle in communication with the ultrasound transducer, the elongate cable bundle passing through the elongate shaft and extending into the handle, wherein the elongate cable bundle passes through a lumen of an electrical noise suppression member therethrough that is secured within the handle, wherein the electrical noise suppression member is configured to provide between 90 ohms and 102 ohms of impedance at a frequency in the range 5 megahertz (MHz) to 10 MHz, relationship is exemplified by $$X_C = \frac{1}{2\pi fC},$$

and wherein a shield layer of the cable bundle is removed from the elongate cable bundle within the handle at a location such that the shield layer does not pass through the lumen of the electrical noise suppression member that is secured within the handle.

19. The catheter of claim 18, wherein the electrical noise suppression member comprises one or both of a material or configuration to suppress electromagnetic interference from the elongate cable bundle.

20. The catheter of claim 18, wherein the electrical noise suppression member comprises one or both of a material or configuration to suppress electromagnetic interference into the elongate cable bundle.

21. The catheter of claim 18, wherein the electrical noise suppression member comprises a ferrite bead.

22. The catheter of claim 18, further including any suitable feature or component of any one of claim 17.

* * * * *